US005837692A

United States Patent [19]
Mercola et al.

[11] Patent Number: 5,837,692
[45] Date of Patent: Nov. 17, 1998

[54] INHIBITION OF THE MITOGENIC ACTIVITY OF PDGF BY MAMMALIAN EGR

[76] Inventors: Dan Mercola; Eileen Adamson, both of P.O. Box 3752, Rancho Santa Fe, Calif. 92067

[21] Appl. No.: 224,482

[22] Filed: Apr. 7, 1994

[51] Int. Cl.⁶ .................................................. A61K 48/00
[52] U.S. Cl. ........................ 514/44; 435/320.1; 435/325; 536/23.5
[58] Field of Search .......................... 514/44; 435/320.1, 435/325; 536/23.5

[56] References Cited

U.S. PATENT DOCUMENTS 5,206,152   4/1993   Sukhatme ............................. 435/69.1

OTHER PUBLICATIONS

Ullrich and Schlessinger, "Signal transduction by receptors with tyrosine kinase activity." *Cell.* 61:203–212 (1990).

Wu, Bei–yue et al., "Isolation of a cDNA clone encoding a zinc finger protein highly expressed in t–leukemia lines." *Blood.* 80(10):2571–2576.

Wu and Adamson, "Inhibition of differentiation in P19 embryonal carcinoma cells by the expression of vectors encoding truncated or antisense EGF receptor." *Devel. Biol.* 159:208–222 (1993).

Mercola, Dan et al., "Rapid, complete and reversible transformation by v–sis precedes irreversible transformation." *Oncogene.* 7:1793–1803 (1992).

Ragona, G. et al., "The transcriptional factor Egr–1 is synthesized by baculovirus–infected insect cells in an active, DNA–binding form." *DNA and Cell Biology.* 10:61–66 (1991).

Christy and Nathans, "DNA binding site of the growth factor–inducible protein Zif268." *Proc. Natl. Acad. Sci. USA.* 86:8737–8741 (1989).

Sukhatme, Vikas P., "Early transcriptional events in cell growth:The Egr family." *J. of The Am. Soc. Nephrol.* 1:859–866 (1990).

McMahon, Andrew P., "Developmental expression of the putative transcription factor Egr–1 suggests that Egr–1 and c–fos are coregulated in some tissues." *Development.* 108:281–287 (1990).

Wilkinson, David G. et al., "Segment–specific expression of a zinc–finger gene in the developing nervous system of the mouse." *Nature.* 337:461–464 (1989).

Sukhatme, Vikas P. et al., "A zinc finger–encoding gene coregulated with c–fos during growth and differentiation, and after cellular depolarization." *Cell.* 53:37–43 (1988).

Klug and Rhodes, "'Zinc fingers':a novel protein motif for nucleic acid recogniton." *TIBS 12.* 464–469 (Dec. 1987).

Gessler, Manfred et al., "Homozygous deletion in Wilms tumours of a zinc–finger gene identified by chromosome jumping." *Nature.* 343:774–778 (1990).

Milbrandt, Jeffrey, "A nerve growth factor–induced gene encodes a possible transcriptional regulatory factor." *Science* 238:797–799 (1987).

Chavrier, Philippe et al., "Characterization of a mouse multigene family that encodes zinc finger structures." *Mol. and Cell. Biol.* 8(3):1319–1326 (1988).

Chavrier, Philippe et al., "A gene encoding a protein with zinc fingers is activated during $G_0/G1_1$ transition in cultured cells." *The EMBO J.* 7(1):29–35 (1988).

Lim, Robert W. et al., "Cloning of tetradecanoyl phorbol ester–induced primary response sequences and their expression in density–arrested Swiss 3T3 cells and a TPA non-proliferative variant." *Oncogene.* 1:263–270 (1987).

Mercola, D., Huang, R.–P., Darland, T., Okamura, D. and Adamson E., "The transcription factor Egr–1 suppresses transformation by the sis oncogene." *Oncogene,* 9:5 (May 1994).

Smeal, Tod et al., "Oncoprotein–mediated signalling cascade stimulates c–Jun activity by phosphorylation of serines 63 and 73." *Mol. and Cell Biol.* 12(8):3507–3513 (1992).

Huang, Ruo–Pan et al., "EGR–1 suppresses the v–sis transformed phenotype." *Mol. and Cell. Diff.* 1(4):377 (1993).

Christy, Barbara A. et al., "A gene activated in mouse 3T3 cells by serum growth factors encodes a protein with 'zinc finger' sequences." *Proc. Natl. Acad. Sci.* 85:7857–7861 (1988).

Crosby, Seth D. et al., "The early response gene NGFI–C encodes a zinc finger transcriptional activator and is a member of the GCGGGGGCG (GSG) element–binding protein family." *Mol. and Cell. Biol.* 11(8):3835–3841 (1991).

Mercola, Dan, "Platelet–derived growth factor, transformation, and antisense." *Gene Regulation:Biology of Antisense RNA and DNA.* 329–353 (1992).

Gashler, Andrea L. et. al., "A novel repression module, an extensive activation domain, and a bipartite nuclear localization signal defined in the immediate–early transcription factor Egr–1." *Mol. And Cell. Biol.* 13(8):4556–4571.

Loren, Joseph J. et al., "Molecular cloning, sequencing, and mapping of EGR2, a human early growth response gene encoding a protein with zinc–binding finger structure." *Proc. Natl. Acad. Sci, USA.* 85:7164–7168 (1988).

Patwardhan, Satish et al., "EGR3, a novel member of the Egr family of genes encoding immediate–early transcription factors." *Oncogene.* 6:917–928 (1991).

Huang et al., Oncogene, 9(5):1367–1377 (1994).

(List continued on next page.)

*Primary Examiner*—Christopher S. F. Low
*Attorney, Agent, or Firm*—Campbell & Flores, LLP

[57] ABSTRACT

This invention is directed to methods for inhibiting the growth in vitro or in an individual of a tumor cell induced by the mitogenic activity of PDGF by transfecting the cell with an expression vector having an expression control sequence operatively linked to a nucleic acid sequence encoding a mammalian EGR, a nucleic acid sequence encoding a fragment of a mammalian EGR comprising the three zinc fingers or a nucleic acid sequence that hybridizes to any of the foregoing nucleic acid sequences under standard hybridization conditions and that encodes a polypeptide having the cell growth-inhibiting activity of Egr-1.

9 Claims, 17 Drawing Sheets

OTHER PUBLICATIONS

Kujubu et al., Journal of Neuroscience Research, 36:58–65 (1993).

Darland et al., Oncogene, 6(8):1367–1376 (1991).

Kim et al., Journal of Biological Chemistry, 269(5):3739–3744 (1994).

Rauscher, F., Advances in Nutrition and Cancer, 23–29 (1993).

Madden et al., Annals of New York Academy of Sciences, 684:75–84 (1993).

Sukhatme, Vickas, Kidney International, 41:550–553 (1992).

Huang et al., Biochemical and Biophysical Research Communications, 200(3):1271–1276 (1994).

Weichselbaum et al., Into. J. Radiation Oncology Biolo. Phys., 30(1):229–234 (1994).

```
Mouse Egr-1 mRNA, complete cds

GGGAGCCGC  CGCCGCGATT  CGCCGCCGCC  GCCAGCTTCC  GCCGCCGCAA  GATCGGCCCC    60
TGCCCCAGCC  TCCGCGGCAG  CCCTGCGTCC  ACCACGGGCC  GCGGCTACCG  CCAGCCTGGG   120
GGCCCACCTA  CACTCCCCGC  AGTGTGCCCC  TGCACCCCGC  ATGTAACCCG  GCCAACCCCC   180
GGCGAGTGTG  CCCTCAGTAG  CTTCGCCCCC  GGCTGCGCC   CACCACCAA   CATCAGTTCT   240
CCAGCTCGCT  GGTCCGGGAT  GGCAGCGGCC  AAGGCCGAGA  TGCAATTGAT  GTCTCCGCTG   300
CAGATCTCTG  ACCCGTTCGG  CTCCTTTCCT  CACTCACCCA  CCATGGACAA  CTACCCCAAA   360
CTGGAGGAGA  TGATGCTGCT  GAGCAACGGG  GCTCCCCAGT  TCCTCGGTGC  TGCCGGAACC   420
CCAGAGGGCA  GCGGCGGTAA  TAGCAGCAGC  AGCACCAGCA  GCGGGGGCGG  TGGTGGGGGC   480
GGCAGCAACA  GCGGCAGCAG  CGCCTTCAAT  CCTCAAGGGG  AGCCGAGCGA  ACAACCCTAT   540
GAGCACCTGA  CCACAGAGTC  CTTTCTGAC   ATCGCTCTGA  ATAATGAGAA  GGCGATGGTG   600
GAGACGAGTT  ATCCCAGCCA  AACGACTCGG  TTGCCTCCCA  TCACCTATAC  TGGCCGCTTC   660
TCCCTGGAGC  CGGCACCCAA  CAGTGGCAAC  ACTTTGTGGC  CTGAACCCCT  TTTCAGCCTA   720
GTCAGTGGCC  TCGTGAGCAT  GACCAATCCT  CCGACCTCTT  CATCCTCGGC  GCCTTCTCCA   780
GCTGCTTCAT  CGTCTTCCTC  TGCCTCCCAG  AGCCCCGCCC  CCACCTTTC   CGTGCCGTCC   840
AACGACAGCA  GTCCCATCTA  CTCGGCTGCG  CCCACCTTTC  CTACTCCCAA  CACTGACATT   900
TTTCCTGAGC  CCCAAAGCCA  GGCCTTTCCT  GGCTCGGCAG  GCACAGCCTT  GCAGTACCCG   960
CCTCCTGCCT  ACCCTGCCAC  CAAAGGTGGT  TTCCAGGTTC  CCATGATCCC  TGACTATCTG  1020
TTTCCACAAC  AACAGGGAGA  CCTGAGCCTG  GGCACCCCAG  ACCAGAAGCC  CTTCCAGGGT  1080
CTGGAGAACC  GTACCCAGCA  GCCTTCGCTC  ACTCCACTAT  CCACTATTAA  AGCCTTCGCC  1140
ACTCAGTCGG  GCTCCCAGGA  CTTAAAGGCT  CTTAATACCA  CCTACCAATC  CCAGCTCATC  1200
AAACCCAGCC  GCATGCGCAA  GTACCCCAAC  CGGCCCAGCA  AGACACCCCC  CCATGAACGC  1260
CCATATGCTT  GCCCTGTCGA  GTCCTGCGAT  CGGCGCTTTT  CGCGCTCGGA  TGAGCTTACC  1320
CGCCATATCC  GCATCCACAC  AGGCCAGAAG  CCCTTCCAGT  GTCGAATCTG  CATGCGTAAC  1380
TTCAGTCGTA  GTGACCACCT  TACCACCCAC  ATCCGCACCC  ACACAGGCGA  GAAGCCTTTT  1440
GCCTGTGACA  TTTGTGGGAG  GAAGTTTGCC  AGGAGTGATG  AACGCAAGAG  GCATACCAAA  1500
```

FIG. 2A-1

```
ATCCATTTAA GACAGAAGGA CAAGAAAGCA GACAAAAGTG TGGTGGCCTC CCCGGCTGCC 1560
TCTTCACTCT CTTCTTACCT ATCCCCAGTG GCTACCTCCT ACCCATCCCC TGCCACCACC 1620
TCATTCCCAT CCCCTGTGCC CACTTCCTAC TCCTCTCCTG GCTCCTCCAC CTACCCATCT 1680
CCTGCGCACA GTGGCTTCCC GTCGCCGTCA GTGGCCACCA CCTTTGCCTC CGTTCCACCT 1740
GCTTTCCCCA CCCAGGTCAG CAGCTTCCCG TCTGCGGGCG TCAGCAGCTC CTTCAGCACC 1800
TCAACTGGTC TTTCAGACAT GACAGCGACC TTTTCTCCCA GGACAATTGA AATTTGCTAA 1860
AGGGAATAAA AGAAAGCAAA GGGAGAGGCA GGAAAGACAT AAAAGCACAG GAGGGAAGAG 1920
ATGGCCGCAA GAGGCCCAC CTCTTAGGTC AGATGGAAGA TCTCAGAGCC AAGTCCTTCT 1980
ACTCACGAGT AGAAGGACCG TTGGCCAACA GCCCTTTCAC TTACCATCCC TGCCTCCCCC 2040
GTCCTGTTCC CTTTGACTTC AGCTGCCTGA AACAGCCATG TCCAAGTTCT TCACCTCTAT 2100
CCAAAGGACT TGATTTGCAT GGTATTGGAT AAATCATTTC AGTATCCTCT CCATCACATG 2160
CCTGGCCCTT GCTCCCCTCA GCGCTAGACC ATCAAGTTGG CATAAAGAAA AAAAAATGGG 2220
TTTGGGCCCT CAGAACCCTG CCCTGCATCT TTGTACAGCA TCTGTGCCAT GGATTTGTT 2280
TTCCTTGGGG TATTCTTGAT GTGAAGATAA TTTGCATACT CTATTGTATT ATTTGGAGTT 2340
AAATCCTCAC TTTGGGGGAG GGGGAGCAA AGCCAAGCAA ACCAATGATG ATCCTCTATT 2400
TTGTGATGAC TCTGCTGTGA CAGCTTGTTT GAAGCATTTT TTTTTTCAAG CAGCAGTCCT 2460
AGTATTAAAC TGGAGCATGT GTCAGAGTGT TGTTCCGTTA ATTTGTAAA TACTGCTCG 2520
ACTGTAACTC TCACATGTGA CAAAGTATGG TTTGTTTGGT TGGGTTTTGT TTTTGAGAAT 2580
TTTTTTGCCC GTCCCTTTGG TTTCAAAAGT TTCACGTCTT GGTGCCTTT GTGTGACACG 2640
CCTTCCGATG GCTTGACATG CGCAGATGTG AGGGACACGC TCACCTTAGC CTTAAGGGGG 2700
TAGGAGTGAT GTGTTGGGGG AGGCTTGAGA GCAAAAACGA GGAAGAGGGC TGAGCTGAGC 2760
TTTCGGTCTC CAGAATGTAA GAAGAAAAAA TTTAAACAAA AATCTGAACT CTCAAAAGTC 2820
TATTTTTCTA AACTGAAAAT GTAAATTTAT ACATCTATTC AGGAGTTGGA GTGTTGTGGT 2880
TACCTACTGA GTAGGCTGCA GTTTTTGTAT GTTATGAACA TGAAGTTCAT TATTTGTGG 2940
TTTTATTTTA CTTTGTACTT GTGTTTGCTT AAACAAAGTA ACCTGTTTGG CTTATAAACA 3000
CATTGAATGC GCTCTATTGC CCATGGGATA TGTGGTGTGT ATCCTTCAGA AAAATTAAAA 3060
GGAAAAAT                                                         3068
```

FIG. 2A-2

Mouse Egr-1 mRNA, complete cds

```
  M  M  L  L  S  N  G  A  P  Q  F  L  G  A  A  G  T  P  E  G
  ATGATGCTGCTGAGCAACGGGGCTCCCCAGTTCCTCGGTGCCGCTGGCACCCCAGAGGGC    429

S  G  G  N  S  S  S  T  S  S  G  G  G  G  G  G  G  S  N
  AGCGGCGGTAATAGCAGCAGCACCAGCAGCGGGGGTGGTGGGGGGGGCAGCAAC          489

S  G  S  S  A  F  N  P  Q  E  P  S  E  Q  P  Y  E  H  L
  AGCGGGCAGCAGCGCCTTCAATCCTCAAGGGGAGCCGAGCGAACAACCCTATGAGCACCTG   549

T  T  E  S  F  S  D  I  A  L  N  N  E  K  A  M  V  E  T  S
  ACCACAGAGTCCTTTTCTGACATCGCTCTGAATAATGAGAAGGCGATGGTGGAGACGAGT    609

Y  P  S  Q  T  T  R  L  P  P  I  T  Y  T  G  R  F  S  L  E
  TATCCCAGCCAAACGACTCGGTTGCCTCCCATCACCTATACTGGCCGCTTCTCCCTGGAG    669

P  A  P  N  S  G  N  T  L  W  P  E  P  L  F  S  L  V  S  G
  CCCGCACCCAACAGTGGCAACACTTTGTGCCTGAACCCCTTTTCAGCCTAGTCAGTGGC     729

L  V  S  M  T  N  P  P  T  S  S  S  A  P  S  P  A  A  S
  CTCGTGAGCATGACCAATCCTCCGACTCTTCATCCTCGGCCTTCTCCAGCTGCTTCA       789

S  S  S  A  S  Q  S  P  P  L  S  C  A  V  P  S  N  D  S
  TCGTCTTCCTCTGCCTCCCAGAGCCCTGAGCTGTCCGTCCAACGACAGC               849

S  P  I  Y  S  A  A  P  T  F  P  T  P  N  T  D  I  F  P  E
  AGTCCCATCTACTCGGCTGCCGCCACTTTCCTACTCCCAACACTGACATTTTCCTGAG      909
```

FIG. 2B-1

```
P  Q  S  Q  A  F  P  G  S  A  G  T  A  L  Q  Y  P  P  P  A
CCCCAAAGCCAGGCCTTTCCTGGCTCGGCCAGGCACAGCCTTGCAGTACCCGCCTCCTGCC                 969

Y  P  A  T  K  G  F  Q  V  P  M  I  P  D  Y  L  F  P  Q
TACCCTGCCACCAAAGGTGGTTTCCAGGTTCCCATGATCCCTGACTATCTGTTTCCACAA                 1029

Q  Q  G  D  L  S  L  G  T  P  D  Q  K  P  F  Q  G  L  E  N
CAACAGGGAGACCTGAGCCTGGGCACCCCAGACCAAGCCCTTCCAGGGTCTGGAGAAC                   1089

R  T  Q  Q  P  S  L  T  P  L  S  T  I  K  A  F  A  T  Q  S
CGTACCCAGCAGCCTTCGCTCACTCCACTTAAAGCCTTCGCCACTCAGTCG                          1149

G  S  Q  D  L  K  A  L  N  T  T  Y  Q  S  L  I  K  P  S
GGCTCCCAGGACTTAAAGGCTCTTAATACCACCTACCAATCCCAGCTCATCAAACCCAGC                 1209

R  M  R  K  Y  P  N  R  P  S  K  T  P  P  H  E  R  P  Y  A
CGGATGCGCAAGTACCCCAACCGGCCCAGCAAGACACCCCCATGAACGCCCATATGCT                   1269

C  P  V  E  S  C  D  R  R  F  S  R  S  D  E  L  T  R  H  I
TGCCCTGTCGAGTCCTGCGATCGCCGCTTTTCTCGCTCGGATGAGCTTACCCGCCATATC                 1329

R  I  H  T  G  Q  K  P  F  Q  C  R  I  C  M  R  N  F  S  R
CGCATCCACACAGGCCAGAAGCCCTTCCAGTGTCGAATCTGCATGCGTAACTTCAGTCGT                 1389

S  D  H  L  T  T  H  I  R  T  H  T  G  E  K  P  F  A  C  D
AGTGACCACCTTACCACCCACATCCGCACCCACACAGGGCGAGAAGCCTTTTGCCTGTGAC                1449

```
ATTTGTGGGAGGAAGTTTGCCAGGAGTGATGAACGCAAGAGGCATACCAAATCCATTTA      1509

R  Q  K  D  K  K  A  D  K  S  V  V  A  S  P  A  A  S  S  L
AGACAGAAGGACAAGAAAGCAGACAAAAGTGTGGTGGCCTCCCCGGCTGCCTCTTCACTC    1569

S  S  Y  P  S  P  V  A  T  S  Y  P  S  P  A  T  T  S  F  P
TCTTCTTACCCATCCCCAGTGGCTACCTCCTACCCCTGCCACCACCTCATTCCCA         1629

S  P  Y  P  T  S  Y  S  S  P  G  S  S  T  Y  P  S  P  A  H
TCCCCTGTGCCCACTTCCTACTCCTCCCTGGCTCCTCCACTACCCATCTCCTGCGCAC      1689

S  G  F  P  S  P  S  V  A  T  F  A  S  V  P  P  A  F  P
AGTGGCTTCCCGTCGCCGTCAGTGGCCACCTTTGCCTCCGTTCCACCTGCTTTCCCC       1749

T  Q  V  S  S  F  P  S  A  G  V  S  S  F  S  T  G
ACCCAGTCAGCAGCTTCCCGTCTGCGGGCGTCAGCAGCTCCTTCAGCACCTCAACTGGT     1809

L  S  D  M  T  A  T  F  S  P  R  T  I  E  I  C  *
CTTTCAGACATGACAGCGACCTTTCTCCCAGGACAATTGAAATTTGCTAAAGGGAATAA     1869
```

FIG. 2C

```
CCGCAGAACT  TGGGGAGCCG  CCGCCGCCAT  CCGCCGCCGC  AGCCAGCTTC  CGCCGCCGCA
GGACCGGCCC  CTGCCCCAGC  CTCCGCCAGC  GCGGCCGTC   CACGCCCGCC  CGGCCCCAGG
GCGAGTCGGG  GTCGCCGCCT  GCACGCTTCT  CAGTGTTCCC  CGCCCCCGC   ATGTAACCCG
GCCAGCCCC   CGCAACGGTG  TCCCCTGCAG  CTCCAGCCCC  GGGCTGCACC  CCCCCGCCCC
GACACCAGCT  CTCCAGCCTG  CTCGTCCAGG  ATGGCCGCGG  CCAAGGCCGA  GATGCAGCTG
ATGTCCCCGC  TGCAGATCTC  TGACCCGTTC  GGATCCTTTC  CTCACTCGCC  CACCATGGAC
AACTACCCTA  AGCTGGAGGA  GATGATGCTG  CTGAGCAACG  GGGCTCCCCA  GTTCCTCGGC
GCCGCCGGGG  CCCCAGAGGG  CAGCGGGCAG  AACAGCAGCA  GCAGCAGCAG  CGGGGGCGGT
GGAGGCGGCG  GGGCGGCAG   CAACAGCAGC  AGCAGCAGCA  GCACCTTCAA  CCCTCAGGCG
GACACGGGCG  AGCAGCCCTA  CGAGCACCTG  ACCGCAGAGT  CTTTTCCTGA  CATCTCTCTG
AACAACGAGA  AGGTGCTGGT  GGAGACCAGT  TACCCCAGCC  AAACCACTCG  ACTGCCCCC
ATCACCTATA  CTGGCCGCTT  TTCCCTGGAG  CCTGCACCCA  ACAGTGGCAA  CACCTTGTGG
CCCGAGCCCC  TCTTCAGCTT  GGTCAGTGGC  CTAGTGAGCA  TGACCAACCA  ACCGGCCTCC
TCGTCCTCAG  CACCATCTCC  AGCGGCCTCC  TCCGCCTCCG  CCTCCCAGAG  CCCACCCCTG
AGCTGCGCAG  TGCCATCCAA  CGACAGCAGT  CCCATTTACT  CAGCGGCACC  CACCTTCCCC
ACGCCGAACA  CTGACATTTT  CCCTGAGCCA  CAAAGCCAGG  CCTTCCCGGG  CTCGGCAGGG
ACAGCGCTCC  AGTACCCGCC  TCCTGCCTAC  CCTGCCGCCA  AGGGTGGCTT  CCAGGTTCCC
ATGATCCCCG  ACTACCTGTT  TCCAGCAGCAG  CAGGGGGATC  TGGGCCTGGG  CACCCCAGAC
```

FIG. 3A-1

```
CAGAAGCCCT  TCCAGGGCCT  GGAGAGCCGC  ACCCAGCAGC  CTTCGCTAAC  CCCTCTGTCT
ACTATTAAGG  CCTTTGCCAC  TCAGTCGGGC  TCCCAGGACC  TGAAGGCCCT  CAATACCAGC
TACCAGTCCC  AGCTCATCAA  ACCCAGCCGC  ATGCGCAAGT  ATCCCAACCG  GCCAGCAAG
ACGCCCCCCC  ACGAACGCCC  TTACGCTTGC  CCAGTGGAGT  CCTGTGATCG  CCGCTTCTCC
CGCTCCGACG  AGCTCACCCG  CCACATCCGC  ATCCACACAG  GCCAGAAGCC  CTTCCAGTGC
CGCATCTGCA  TGCGCAACTT  CAGCCGCAGC  GACCACCTCA  CCACCCACAT  CCGCACCCAC
ACAGGCGAAA  AGCCCTTCGC  CTGGACATC  TGTGGAAGAA  AGTTTGCCAG  GAGCGATGAA
CGCAAGAGGC  ATACCAAGAT  CCACTTGCGG  CAGAAGGACA  AGAAAGCAGA  CAAAAGTGTT
GTGGCCTCTT  CGGCCACCTC  CTCTCTCT  TCCTACCCGT  CCCGGTTGC  TACCTCTTAC
CCGTCCCCGG  TTACTACCTC  TTATCCATCC  CCGGCCACCA  CCTCATACCC  ATCCCCTGTG
CCCACCTCCT  TCTCCTCTCC  CGGCTCCTCG  ACCTACCCAT  CCCCTGTGCA  CAGTGGCTTC
CCCTCCCCGT  CGGTGGCCAC  CACGTACTCC  TCTGTTCCCC  CTGCTTTCCC  GGCCCAGGTC
AGCAGCTTCC  CTTCCTCAGC  CTTCCTCAGC  TCCTTCAGCG  CCTCCACAGG  GCTTTCGGAC
ATGACAGCAA  CCTTTTCTCC  CAGGACAATT  GAAATTTGCT  AAAGGGAAAG  GGGAAAGAAA
GGGAAAAGGG  AGAAAAAGAA  ACACAAGAGA  CTTAAAGGAC  AGGAGGAGGA  GATGGCCATA
GGAGAGGAGG  GTTCCTCTTA  GGTCAGATGG  AGGTTCTCAG  AGCCAAGTCC  TCCCTCTA
CTGGAGTGGA  AGGTCTATTG  GCCAACAATC  CTTTCTGCCC  ACTTCCCCTT  CCCAATTAC
```

FIG. 3A-2

```
TATTCCCTTT GACTTCAGCT GCCTGAAACA AGTTCTTCAC CTCTATCCAA
AGAACTTGAT TTGCATGGAT TTTGGATAAA TCATTTCAGT ATCATCTCCA
GACCCCTTGC TCCCTTCAAT GCTAGAAAAT CGAGTTGGCA AAATGGGGTT TGGGCCCCTC
AGAGCCCTGC CCTGCACCCT TGTACAGTGT CTGTGCCATG GATTTCGTTT TTCTTGGGGT
ACTCTTGATG TGAAGATAAT TTGCATATTC TATTGTATTA TTTGGAGTTA GGTCCTCACT
TGGGGGAAAA AAAAAAAAAA AAGCCAAGCA AACCAATGGT GATCCTCTAT TTTGTGATGA
TGCTGTGACA ATAAGTTTGA ACCTTTTTTT TTGAAACAGC AGTCCCAGTA TTCTCAGAGC
ATGTGTCAGA GTGTTGTTCC GTTAACCTTT TTGTAAATAC TGCTTGACCG TACTCTCACA
TGTGGCAAAA TATGGTTTGG TTTTTCTTTT TTTTTTTTGA AAGTGTTTTT TCTTCGTCCT
TTTGGTTTAA AAAGTTTCAC GTCTTGGTGC CTTTTGTGTG ATGCCCCTTG CTGATGGCTT
GACATGTGCA ATTGTGAGGG ACATGCTCAC CTCTAGCCTT AAGGGGGGCA GGGAGTGATG
ATTTGGGGGA GGCTTTGGGA GCAAAATAAG GAAGAGGGCT GAGCTGAGCT TCGGTTCTCC
AGAAATGTAAG AAAACAAAAT CTAAAACAAA ATCTGAACTC TCAAAAGTCT ATTTTTTAA
CTGAAAATGT AAATTTATAA ATATATTCAG GAGTTGGAAT GTTGTAGTTA CCTACTGAGT
AGGCGGCGAT TTTTGTATGT TATGAACATG CAGTTCATTA TTTTGTGGTT CTATTTTACT
TTGTACTTGT GTTTGCTTAA ACAAGTGAC TGTTTGGCTT ATAAACACAT TGAATGCGCT
TTATTGCCCA TGGGATATGT GGTGTATATC CTTCCAAAAA ATTAAAACGA AAATAAAGTA
GCTGCGATTG GG
```

FIG. 3B

MAAAKAEMQL MSPLQISDPF GSFPHSPTMD NYPKLEEMML LSNGAPQFLG AAGAPEGSGS
NSSSSSGGG GGGGGGSNSS SSSSTFNPQA DTGEQPYEHL TAESFPDISL NNEKVLVETS
YPSQTTRLPP ITYTGRFSLE PAPNSGNTLW PEPLFSLVSG LVSMTNPPAS SSSAPSPAAS
SASASQSPPL SCAVPSNDSS PIYSAAPTFP TPNTDIFPEP QSQAFPGSAG TALQYPPPAY
PAAKGGFQVP MIPDYLFPQQ QGDLGLGTPD QKPFQGLESR TQQPSLTPLS TIKAFATQSG
SQDLKALNTS YQSQLIKPSR MRKYPNRPSK TPPHERPYAC PVESCDRRFS RSDELTRHIR
IHTGQKPFQC RICMRNFSRS DHLTTHIRTH TGEKPFACDI CGRKFARSDE RKRHTKIHLR
QKDKKADKSV VASSATSSLS SYPSPVATSY PSPVTTSYPS PATTSYPSPV PTSFSSPGSS
TYPSPVHSGF PSPSVATTYS SVPPAFPAQV SSFPSSAVTN SFSASTGLSD MTATFSPRTI
EIC

FIG. 3C

```
                                                               MetThr
TCTGACACTCCAGGTAGCGAGGAGTTGGGTCTCCAGGTTGTGCGAGGAGCAAATGATGA         60

AlaLysAlaValAspLysIleProValThrLeuSerGlyPheValHisGlnLeuSerAsp
CGCCAAGGCCGTAGACAAAATCCCAGTAACTCTCAGTGGTTTTGTGCACCAGCTGTCTG       120

AsnIleTyrProValGluAspLeuAlaAlaAlaThrSerValThrIlePheProAsnAlaGlu
ACAACATCTACCCGGTGGAGGACCTCGCCGCCGCCACGTCGGTGACCATCTTTCCAATGCCG   180

LeuGlyProPheAspGlnMetAsnGlyValAlaAlaGlyAspGlyMetIleAsnIleAsp
AACTGGGAGGCCCCTTTGACCAGATGAACGGAGTGGCCGGAGATGGCATGATCAACATTG     240

MetThrGlyGluLysArgSerLeuAspLeuProTyrProSerSerPheAlaProValSer
ACATGACTGGAGAAGAGAGTCGTTGGATCTCCCATATCCCAGCAGCTTTGCTCCCGTCT      300

AlaProArgAsnGlnThrPheThrTyrMetGlyLysPheSerIleAspProGlnTyrPro
CTGCACCTAGAAACCAGACCTTCACTTACATGGGCAAGTTCTCCATTGACCCACAGTACC    360

GlyAlaSerCysTyrProGluGlyIleIleAsnIleValSerAlaGlyIleLeuGlnGly
CTGGTGCCAGCTGCTACCCAGAAGGCATAATCAATCAATATTGTGAGTGCAGGCATCTTGCAAG  420

ValThrSerProAlaSerThrThrAlaSerSerValThrSerAlaSerProAsnPro
GGGTCACTTCCCCAGCTTCAACCACCGCCTCATCCAGCGTCACCTCTGCCTCCCCAACC      480

LeuAlaThrGlyProLeuGlyValCysThrMetSerGlnThrGlnProAspLeuAspHis
CACTGGCCACAGGACCCCTGGGTGTGTGCACCATGTCCCAGACCCAGCCTGACCTGGACC     540
```

FIG. 4A-1

```
LeuTyrSerProProProProProTyrSerGlyCysAlaGlyAspLeuTyrGln                                          600
ACCTGTACTCTCCGCCACCGGCCTCCTCCTTATTCTGGTGTGCAGGAGACCTCTACC

AspProSerAlaPheLeuSerAlaAlaThrThrSerThrSerSerSerLeuAlaTyrPro                                    660
AGGACCCCTTCTGCGTTCCTGTCAGCAGCCACCACCTCCACCTCTTCCTCTGCCTACC

ProProProSerTyrTyrProSerProLysProAlaThrAspProGlyLeuPheProMetIle                                 720
CACCACCTCCTTCCTATCCATCCCCAAGCCAGCCACGGACCCAGGTCTCTTCCAATGA

ProAspTyrProGlyPhePheProSerGlnCysGlnArgAspLeuHisGlyThrAlaGly                                    780
TCCCAGACTATCCTGGATTCTTTCCATCTCAGTGCCAGAGAGACCTACATGGTACAGCTG

ProAspArgLysProPheProCysProLeuAspThrLeuArgValProProProLeuThr                                    840
GCCCAGACCGTAAGCCCCTTTCCCTGCCCTTGACACCCTGAGGGTGCCCCCCTCCACTCA

ProLeuSerThrIleArgAsnPheThrLeuGlyGlyProSerAlaGlyMetThrGlyPro                                    900
CTCCACTCTCTACAATCCGTAACTTTACCCTGGGGGGCCCCAGTGCTGGGATGACCGGAC

GlyAlaSerGlyGlySerGluGlyProArgLeuProGlySerSerAlaAlaAlaAlaAla                                    960
CAGGGGCCAGTGGAGGCAGCGAGGGACCCCGGCTGCCTGGTAGCAGCTCAGCAGCAGCAG

AlaAlaAlaAlaAlaAlaTyrAsnProHisHisLeuProLeuArgProIleLeuArgPro                                    1020
CAGCCGCCGCCGCCAACGCCCTATAACCCACACCACCTGCCACTGCGCCCATTCTGAGGC

ArgLysTyrProAsnArgProSerLysThrProValHisGluArgProTyrProCysPro                                    1080
CTCGCAAGTACCCCAACAGACCCAGCAAGACCCCGGTGCACGAGAGGCCCTACCCGTGCC
```

FIG. 4A-2

```
AlaGluGlyCysAspArgArgPheSerArgArgSerAspGluLeuThrArgHisIleArgIle
CAGCAGAAGGCTGCGACCGGTTCTCCCGCTCTGACGAGCTGACACGGCACATCCGAA        1140

HisThrGlyHisLysProPheGlnCysArgIleCysMetArgAsnPheSerArgSerAsp
TCCACACTGGGCATAAGCCCCTTCCAGTGTCGGATCTGCATGCGCAACTTCAGCCGCAGTG    1200

HisLeuThrThrHisIleArgThrHisThrGlyGluLysProPheAlaCysAspTyrCys
ACCACCTCACCACCCATATCCGCACCCACACCGGTGAGAAGCCCTTCGCCTGTGACTACT     1260

GlyArgLysPheAlaArgSerAspGluArgLysArgHisThrLysIleHisLeuArgGln
GTGGCCGAAAGTTTGCCCGGAGTGATGAGAGAAGCCGCCACACCAAGATCCACCTGAGAC     1320

LysGluArgLysSerSerAlaProSerAlaSerValProAlaProSerCys
AGAAAGAGCGGAAAAGCAGTGCCCCCTCTGCCAGCCCCTCTACAGCCTCCT              1380

SerGlyGlyValGlnAlaTrpGlyTyrProValGlnGln***
GCTCTGGGGGGTGCAGGCCTGGGGGGTACCCTGTGCAGCAGTAACAGCAGCAGTCTTGGC     1440
```

FIG. 4B

|          10 |         20 |         30 |         40 |         50 |     |
| 1234567890 | 1234567890 | 1234567890 | 1234567890 | 1234567890 |     |
| GATCAATACT | GAGGCCGCGT | CGACCCCTT  | GAGCCGAGAC | CCCCCCCCAG | 50  |
| CCCAGCCCCC | ACCCCACCCC | CCGCACACGC | CCACCCCCC  | CCACGACCCA | 100 |
| GCCTCATACC | GCACCAGCTG | AGGCACCCAA | GAGGATTACC | CCCTGGGGCC | 150 |
| CTCTCCCGCC | CCCCAAAAAA | GAGAAGATCC | CCTCTCCTGG | CCCATCCCTT | 200 |
| CCCTTCTTCC | CTCCCCCCTC | CCCCCGAACT | TTCCCTCTCG | CATGCTTTTC | 250 |
| CCCTGCACCA | CGGATCGCCT | CTCGGATGCC | GCTTGCCTGG | AAGCTGCGTT | 300 |
| AGGAGCGAGC | GGCGGCGGTG | GCGGCGGTGG | CGGCGGCGGC | GGCAGCTCGG | 350 |
| GAGTGCTATG | ACCGGCAAAC | TCGCCGAGAA | GCTGCCGGTG | ACCATGAGCA | 400 |

Met ThrGlyLysL euAlaGluLy sLeuProVal ThrMetSerS
GTTTGCTAAA CCAACTGCCT GACAATCTGT ACCCGAGGA GATCCCCAGC     450
erLeuLeuAs nGlnLeuPro AspAsnLeuT yrProGluGl uIleProSer
GCGCTCAACC TCTTCTCCGG CAGCAGCGAC TCGGTAGTCC ATTACAATCA     500
AlaLeuAsnL euPheSerGl ySerSerAsp SerValValH isTyrAsnGl
GATGGCTACA GAGAATGTAA TGGACATCGG TCTGACCAAC GAGAAGCCCA     550
nMetAlaThr GluAsnValM etAspIleGl yLeuThrAsn GluLysProA
ACCCGGAACT CTCTTACTCC GGCTCCTTCC AGCCAGCCCC CGGAACAAG      600
snProGluLe uSerTyrSer GlySerPheG lnProAlaPr oGlyAsnLys
ACCGTGACCT ACTTGGGAAA GTTCGCCTTC GACTCCCCTT CCAACTGGTG     650
ThrValThrT yrLeuGlyLy sPheAlaPhe AspSerProS erAsnTrpCy
CCAGGACAAC ATCATTAGCC TCATGAGCGC CGGCATCTTG GGGGTGCCCC     700
sGlnAspAsn IleIleSerL euMetSerAl aGlyIleLeu GlyValProP
CGGCTTCAGG GGCGCTAAGC ACGCAGACGT CCACGGCCAG CATGGTGCAG     750
roAlaSerGl yAlaLeuSer ThrGlnThrS erThrAlaSe rMetValGln
CCACCGCAGG GTGACGTGGA GGCCATGTAT CCCGCGCTAC CCCCCTACTC     800
ProProGlnG lyAspValGl uAlaMetTyr ProAlaLeuP roProTyrSe
CAACTGCGGC GACCTCTACT CAGAGCCCGT GTCTTCCAC GACCCCCAGG      850
rAsnCysGly AspLeuTyrS erGluProVa lSerPheHis AspProGlnG
GCAATCCCGG GCTCGCCTAT TCCCCCCAGG ATTACCAATC GGCCAAGCCG     900
lyAsnProGl yLeuAlaTyr SerProGlnA spTyrGlnSe rAlaLysPro
GCGTTGGACA GCAATCTCTT CCCCATGATT CCTGACTACA ACCTCTACCA     950
AlaLeuAspS erAsnLeuPh eProMetIle ProAspTyrA snLeuTyrHi

FIG. 5A

|  | 10 | 20 | 30 | 40 | 50 |  |
|---|---|---|---|---|---|---|
|  | 1234567890 | 1234567890 | 1234567890 | 1234567890 | 1234567890 |  |
|  | CCACCCCAAC | GACATGGGCT | CCATTCCGGA | GCACAAGCCC | TTCCAGGGCA | 1000 |
|  | sHisProAsn | AspMetGlyS | erIleProGl | uHisLysPro | PheGlnGlyM |  |
|  | TGGACCCCAT | CCGGGTCAAC | CCGCCCCCTA | CTACCCCTCT | GGAGACCATC | 1050 |
|  | etAspProIl | eArgValAsn | ProProProT | hrThrProLe | uGluThrIle |  |
|  | AAGGCATTCA | AAGACAAGCA | GATCCACCCG | GGCTTTGGCA | GCCTGCCCCA | 1100 |
|  | LysAlaPheL | ysAspLysGl | nIleHisPro | GlyPheGlyS | erLeuProGl |  |
|  | GCCGCCGCTC | ACCCTCAAGC | CCATCCGGCC | CCGCAAGTAC | CCCAACCGGC | 1150 |
|  | nProProLeu | ThrLeuLysP | roIleArgPr | oArgLysTyr | ProAsnArgP |  |
|  | CTAGCAAGAC | ACCGCTCCAC | GAACGGCCCC | ACGCGTGCCC | GGCCGAGGGC | 1200 |
|  | roSerLysTh | rProLeuHis | GluArgProH | isAlaCysPr | oAlaGluGly |  |
|  | TGCGACCGCC | GTTTCAGCCG | TTCGGACGAG | CTGACCCGGC | ACCTGCGCAT | 1250 |
|  | CysAspArgA | rgPheSerAr | gSerAspGlu | LeuThrArgH | isLeuArgIl |  |
|  | CCACACGGGC | CACAAGCCCT | TCCAGTGCCG | GATCTGCATG | CGGAGCTTCA | 1300 |
|  | eHisThrGly | HisLysProP | heGlnCysAr | gIleCysMet | ArgSerPheS |  |
|  | GCCGCAGCGA | CCACCTCACC | ACTCACATCC | GCACTCATAC | GGGCGAGAAG | 1350 |
|  | erArgSerAs | pHisLeuThr | ThrHisIleA | rgThrHisTh | rGlyGluLys |  |
|  | CCCTTTGCCT | GCGAGTTCTG | CGGGCGCAAG | TTTGCGCGCA | GCGACGAGCG | 1400 |
|  | ProPheAlaC | ysGluPheCy | sGlyArgLys | PheAlaArgS | erAspGluAr |  |
|  | CAAGCGCCAC | GCCAAGATCC | ACCTCAAGCA | AAAGGAGAAG | AAGGCGGAGA | 1450 |
|  | gLysArgHis | AlaLysIleH | isLeuLysGl | nLysGluLys | LysAlaGluL |  |
|  | AGGGCGGTGC | ACCCTCTGCA | TCCTCGGCGC | CCCCCGTGTC | GCTGGCCCCC | 1500 |
|  | ysGlyGlyAl | aProSerAla | SerSerAlaP | roProValSe | rLeuAlaPro |  |
|  | GTGGTCACCA | CCTGCGCCTG | AGGATCGGGC | CCCCAGATCC | CCACTTTTCC | 1550 |
|  | ValValThrT | hrCysAla.. | . |  |  |  |
|  | CCTCCAGTGC | CTCCCGGCTG | CTAGCCTGAA | AGCAGCGGGA | AAGCCAGCCA | 1600 |
|  | CGGAGGCGTA | GGGGCCGCGC | CCTGGCCTCT | CCATGGACGT | GCGGCCCCTT | 1650 |
|  | GCTTCCCCTT | CGATGCCCCC | GGTTCCCAAC | CTTTCACGCC | GGCCAGCGGT | 1700 |
|  | CAGGGCCAG | GGCTGGAGCC | GCCTTCCCCT | CGCGGTCCCC | CACTTAGCCA | 1750 |
|  | AGGCGTGGGG | GCGGAAAGGT | GGCGTCTAGC | CCGCTTTGTT | CAGTTCGGAT | 1800 |
|  | CGCCTTGATC | CAGGGGCCGC | CGGGCCGCGC | CAAGGACCTG | CAAGGGACTG | 1850 |
|  | AAGGCGGAGC | CCATCCAACC | CTCGCCCGAC | CCAAACACCT | CATTGTTTCC | 1900 |

FIG. 5B

```
          10         20         30         40         50
 1234567890 1234567890 1234567890 1234567890 1234567890
CCCACGTCTC CCTCTATACC CCCTCGAAGA CTCGAGAGGG GGAGGGGTA    1950

AGGAGCGCAC CAAAGCGCAG AGCTTGCTGC CCGCCGCACG CACGCGCGCC   2000

TCCGTCCGGG GATGCGCGCG AGTGTGTGCG TGCTCGCGTG TGTGTGTATG   2050

TGTGTGTGTG AGTGTGTGTG TGTGCGCGCG CGCAAGCGTG TGTGTTTAAG   2100

ACTCTTGAGC TGAACTCGGC TGTGTTTACC CCAAACTCTT CCCCACCTCG   2150

GGTCCCCAAG CCGCTGGAG ATGTCCCATG CTGGGGGTCC GCACGTGGCT    2200

GGAGGAGGTG GTCTTCCATC CGCTCTGAAA TCATGTTTCT TAGAGAAATG   2250

CCTCGGATGC CGCCGACGCG GTGCTGCTGC CGCCGCTTCG GGTTTGGCCC   2300

CTCAGAACCC CTCCTTTTCT GAGCGCTTCC CTCTTAGGCC TCAGGGCAGT   2350

TTGATCTGTG GGGAGAAAGA GCAGCCATCG CTGAGCCTGC CTTTTAAAAT   2400

ATATGTGTAT TTCCTTAGCC CCACTCTAAG AAATCTATGT TCCTGAGTTT   2450

GCCCCCTGCC CTCCCACTCC TTCCCCTTTT CCCCTCTAAA CCTTCTCCCA   2500

TCTCTTTCAA AATCTTTTCC CAGAAAGGCA GGCTTCAACC AGCCACTCCA   2550

GCTTTGTGTC TTCTCTCAAT TACATAGCAA TTTCTCCTTC CCACCATCAT   2600

GGGAAGCTG GCTCTGCTTT TGCCCTTTGT CATCACCAAC ACAACAGATA    2650

GAATTTAAAT ATAAGTATAT GGTGTGCGTG TGTATGTATG TGTATGTATA   2700

TGCATGCATG TGTATAAAGA TGCACATGCG TACATATACA TAACATACAC   2750

ACAATATGTA TTCCTAGCAA AATAAAATCT CTAAGGTACT TGGTTATCCA   2800

GTGCAGTCCA CCGGAATAAA GAGAATTTGT AGGCGTATAC AGCTTTAAAT   2850
```

FIG. 5C

# INHIBITION OF THE MITOGENIC ACTIVITY OF PDGF BY MAMMALIAN EGR

BACKGROUND OF THE INVENTION

This invention was made partially with government support under NIH-RO1, HD 21957 (EDA), HD 28025 (EDA), and CA 49963 (DAM), awarded by the National Institutes of Health. The government has certain rights in this invention.

This invention relates to the fields of molecular biology and cancer therapy and, in particular, to the suppression of v-sis-dependent transformation by the transcription factor, Egr-1.

V-sis is an oncogene of the simian sarcoma virus. Expression of v-sis in established or primary fibroblast cell lines leads to complete transformation, including tumorigenesis. V-sis encodes a polypeptide that shares over 90% amino acid sequence homology with the mammalian c-sis gene.

The mammalian c-sis gene encodes the B-chain of platelet-derived growth factor (PDGF). PDGF is a 30 kDa protein composed of two chains, the A-chain and the B-chain, linked by disulfide bonds. The chains share considerable sequence homology but are products of separate genes. Mature secreted PDGF also may be composed of two B-chains (predominant in pigs) or two A-chains, thereby defining three "isoforms" of PDGF.

PDGF is a potent mitogenic growth factor which acts on cells bearing the specific membrane-bound receptors. These receptors are most numerous on, but not exclusive to, neuro-ectodermal derivatives such as fibroblasts, smooth muscle cells and glial cells.

A very large body of circumstantial evidence shows that continuous expression of the A- and/or B-chain occurs in numerous human tumor cell lines and primary isolates of human tumors. At least twenty-six human tumor types are known which continuously express A- and/or B-chain dimers, including epithelial tumors. Evidence supports the idea that both autocrine and paracrine mechanisms are important in causing or maintaining the transformed state.

PDGF acts by binding to a receptor on the cell surface. There are two forms of receptors for PDGF called PR-α and PR-β. The two receptors are highly homologous transmembrane tyrosine kinases. Binding of PDGF to its receptor results in activation of a signal transduction pathway. This path ultimately leads to increased and/or activated transcription factors which directly regulate a range of genes. Many genes regulated by PDGF and involved in cell division have been identified.

Since the expression of PDGF transforms cells and promotes the growth of tumors, there is a need for methods of inhibiting its activity. This invention satisfies this need and provides related advantages as well by providing methods of inhibiting the growth of tumor cells induced by the mitogenic activity of PDGF by expressing a mammalian EGR gene, or certain fragments of it, in the transformed cells.

SUMMARY OF THE INVENTION

This invention provides methods for inhibiting the growth of a tumor cell in an individual or a transformed culture cell induced by the mitogenic activity of PDGF by transfecting the cell with a vector comprising an expression control sequence operatively linked to a nucleic acid sequence encoding a mammalian EGR, a nucleic acid sequence encoding a fragment of a mammalian EGR comprising the zinc finger domain or a nucleic acid sequence that hybridizes to any of the foregoing nucleic acid sequences under standard hybridization conditions and that encodes a polypeptide that inhibits the mitogenic activity of PDGF.

This invention also provides expression vectors having an expression control sequence operatively linked to a nucleic acid sequence encoding a fragment of a mammalian EGR consisting essentially of the zinc finger domain, optionally including the remainder of the carboxy-terminal end of the molecule.

This invention further provides methods of inhibiting the growth of a tumor cell in an individual or a transformed culture cell induced by the mitogenic activity of a RTK ligand comprising transfecting the cell with an expression vector having an expression control sequence operatively linked to a nucleic acid sequence encoding a mammalian receptor tyrosine kinase ("RTK") ligand, a nucleic acid sequence encoding a fragment of a mammalian RTK ligand comprising the zinc finger domain or a nucleic acid sequence that hybridizes to any of the foregoing nucleic acid sequences under standard hybridization conditions and that encodes a polypeptide that inhibits the mitogenic activity of PDGF.

BRIEF DESCRIPTION OF THE DRAWINGS

FIG. 2A depicts the nucleotide sequence [SEQ ID NO:1] and FIGS. 2B to 2C depict the deduced amino acid sequence [SEQ ID NO:2] (with the nucleotide sequence) of mouse Egr-1 cDNA.

FIGS. 3A to 3B depict the nucleotide sequence [SEQ ID NO:3] and FIG. 3C depicts the deduced amino acid sequence [SEQ ID NO:4] of human EGR1 cDNA.

FIGS. 4A to 4B depict the nucleotide sequence [SEQ ID NO:5] and deduced amino acid sequence [SEQ ID NO:6] of human EGR2 cDNA.

FIGS. 5A to 5C depict the nucleotide sequence [SEQ ID NO:7] and deduced amino acid sequence [SEQ ID NO:8] of human EGR3 cDNA.

FIG. 5A depicts immunoprecipitation of metabolically-labeled protein analyzed by SDS-PAGE and fluorography: N+ser, NIH3T3 cells stimulated with 20% serum for 50 minutes; NnSER, an NIH3T3 clone after transfection with expression vectors for neo (n)+sis+Egr-1+Rge; NnSR, NIH3T3 cells transfected with neo+sis+Rge. (R and Rge refer to antisense Egr-1 RNA expressed by a stably inserted plasmid designed to transcribe a full-length antisense transcript.) The position of molecular markers is shown with Mr in kDa. FIG. 5B depicts gel retardation assays to show the relative amounts of Egr-1 protein in nuclear extracts. The retarded band of specific, labeled oligonucleotide binding sequence due to the presence of Egr-1 is shown. The other bands are resent in all lanes and are non-specific. FIG. 5C depicts an immunoblot of the Egr-1 protein present in lysates of NIH3T3 cells transfected with v-sis without (NnS), or with antisense Egr-1 (NnSR). The expression of Egr-1 was stimulated by the addition of serum for 50 minutes (lanes 2 & 4). All lanes were equally loaded with protein. FIG. 5D depicts an immunoblot to show the steady-state levels of Egr-1 protein in several transfected cell lines. Lane 3, NnSE are NnS cells that over-express Egr-1: lanes 2, 4 and 5, three different NnS clones that express antisense Egr-1 (NnSR).

DETAILED DESCRIPTION OF THE INVENTION

Figure 1:
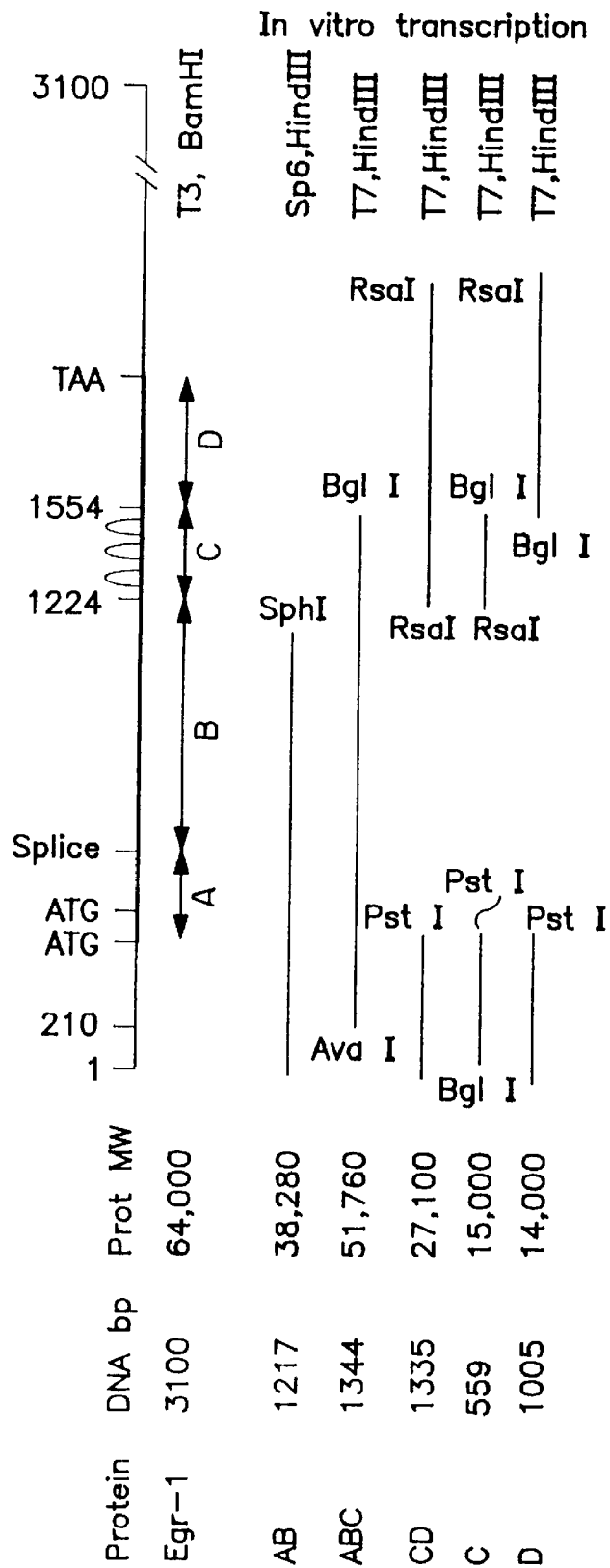
FIG. 1 presents a schematic diagram of the truncated forms of Egr-1 and their calculated molecular weights. Fragments were constructed as described in the Example using standard recombinant DNA techniques. The truncated forms contain the 13 initial amino acids from the first methionine to proline, in order to initiate translation. The fragments were cloned into pGEM-1 (Promega) to effect their synthesis in vitro, and into eukaryotic vectors driven by RSV for expression in NIH3T3 cells. The four principal domains of Egr-1 are designated A, B, C, and D. The DNA-binding zinc-finger domain is indicated (domain C).

This invention results from two discoveries. First, long term expression of the transcription factor Egr-1 inhibits growth of mammalian cells transformed by the v-sis oncogene, which encodes a form of PDGF. Second, the ability to inhibit growth resides in fragments of Egr-1 containing as little as the zinc finger domain of Egr-1.

Mammalian EGR (early growth response) is a transcription factor that stimulates the activity of a number of mammalian genes and inhibits other genes. The mammalian EGRs contain three zinc fingers of the $Cys_2His_2$ class that bind to the GCE site in 5' enhancer region, which has the sequence GCGGGGGCG [SEQ ID NO:9] or GCGT/AGGGCG [SEQ ID NO:10]. However, the functions of EGR are obscure.

Egr-1, a mouse EGR gene, is associated with growth stimulation since it is rapidly induced by many growth factors and other stimuli. It is also known as Krox24, zif268 and TIS8. Typically, stimulation of quiescent cells leads to a transient peak of expression that returns to base values which are low but detectable. This is typical of most of the immediate early growth response genes such as c-fos and c-jun. However, Egr-1 is constitutively expressed in differentiated embryonal carcinoma (EC) cells where evidence supports its role in maintaining the differentiated state. When EC cells are induced to differentiate, the expression of Egr-1 increases markedly.

Egr-1 stimulates the activity of the GCE site in several promoters in transient expression assays. Genes whose transcription has been shown to be inhibited by Egr-1 include the PDGF-A gene (as tested in NIH-3T3 cells), adenosine deaminase (ADA) gene 1 (as tested in murine Cl-1D cells), and the midkine (MK) gene (as tested in P19 cells). Moreover, it appears that Egr-1 can compete with Sp1 in binding to an overlapping consensus binding motif in the promoter region of murine ADA therefore abolishing the function of Sp1. However, in several cell types Egr-1 stimulates the activity of the GC-rich DNA-binding element (GCE) while WT1 inhibits. Madden et al., *Science*, 253:1550 (1991).

The expression of Egr-1 protein in at least two cell types stimulates the activity of a GCE-CAT reporter gene construct in transient expression assays. Unexpectedly, however, in stable v-sis-transformed cells, Egr-1 expression represses transformed growth.

Accordingly, this invention provides methods useful for inhibiting the growth of a tumor cell in a mammal induced by the mitogenic activity of PDGF. Such methods are useful in the therapy of cancer. These methods are useful for inhibiting the mitogenic activity of PDGF in culture cells. The ability to inhibit the activity of PDGF in culture cells is desirable for masking this activity of PDGF and promises to contribute greatly to the understanding of the mechanism of PDGF activity.

The methods of this invention involve transfecting a cell with an expression vector having an expression control sequence operatively linked to a nucleic acid sequence encoding a mammalian EGR, a nucleic acid sequence encoding a fragment of a mammalian EGR comprising the zinc finger domain or a nucleic acid sequence that hybridizes to any of the foregoing nucleic acid sequences under standard hybridization conditions and that encodes a polypeptide that inhibits the mitogenic activity of PDGF.

According to one embodiment of the invention, the method is used to inhibit the growth of a tumor cell in a human. Tumors whose growth can be inhibited by the expression of mammalian EGR include cancers of cells derived from mesoderm such as osteosarcomas and fibrosarcomas; neuro-ectodermal tumors such as glioblastomas; and PDGF-producing epithelial tumors such as pancreatic, breast and lung carcinoma.

According to another embodiment of the invention, the cell is a transformed culture cell such as from human fibrosarcoma cell lines, human osteosarcoma cell lines, human leiomyosarcoma cell lines, human glioblastoma cell lines and v-sis-transformed NIH 3T3 cells.

As used herein, the term "mammalian EGR" refers to a polypeptide of the EGR gene family having activity as a transcription factor. This includes the polypeptides encoded by the mouse Egr-1 gene, the human EGR1 gene, the human EGR2 gene, the human EGR3 gene, the human EGR4 gene and other mammalian EGR genes identifiable as follows. A mammalian EGR is characterized by having 30% overall amino acid sequence identity with at least one of the foregoing mammalian EGRs. It has a zinc finger domain with at least 80% amino acid identity with the zinc finger domain of at least one of the foregoing mammalian EGRs. A mammalian EGR is also characterized by its ability to bind to the GCE site.

The DNA and amino acid sequence of mouse Egr-1 is given in FIG. 2 [SEQ ID NOS:1 and 2]. The DNA and deduced amino acid sequence of human EGR1 is given in FIG. 3 [SEQ ID NOS:3 and 4]. The DNA and deduced amino acid sequence of human EGR2 is given in FIG. 4 [SEQ ID NOS:5 and 6]. The DNA and deduced amino acid sequence of human EGR3 is given in FIG. 5 [SEQ ID NO:7 and 8]. A partial DNA and amino acid sequence of human EGR4 is given in Patwardhan et al., *Oncogene*, 6:917 (1991).

It is recognized that minor modifications can be made to EGR while retaining the growth inhibitory activity of the molecule. Minor modifications include simple substitutions, additions or deletions. Simple substitutions include the substitution of an amino acid for another having a side chain off the alpha carbon of the same class, i.e., non-polar (hydrophobic), neutral, positively charged or negatively charged. These modifications may be introduced deliberately through site-directed mutagenesis, or may be accidental, such as through mutation in hosts having DNA encoding these polypeptides. Any such modified protein can be easily tested for activity in the transformation assay described in the Example, infra.

It has also been discovered that fragments of mammalian EGR containing the zinc finger domain also inhibit the growth of cells induced by the mitogenic activity of PDGF. These fragments are useful in the methods of this invention. The zinc finger domain of EGR contains the three zinc fingers of EGR. The zinc finger domain extends from amino acids 320 to 431 [SEQ ID NO:2] (nucleotides 1215 to 1551 [SEQ ID NO:1]) of mouse Egr-1 (FIG. 2); amino acids 322 to 433 [SEQ ID NO:4] (nucleotides 1234 to 1567 [SEQ ID NO:3]) of human EGR1 (FIG. 3); amino acids 214 to 380 [SEQ ID NO:6] (nucleotides 1023 to 1350 [SEQ ID NO:5]) of human EGR2 (FIG. 4); amino acids 258 to 368 [SEQ ID NO:8] (nucleotides 1132 to 1467 [SEQ ID NO:7]) of human EGR3 (FIG. 5) and the following sequence of EGR4 (Patwardhan et al., supra): RGGKCSTRC FCPRPHAKAFA CPVESCVRS FARSDELNRH LRIHTGHKPF QCRICL- RNFS RSDHLTTHVR THTGEKPFAC DVCGRRFARS DEKKRHSKVH LRQKARAEER [SEQ ID NO:11]. The zinc finger domain of other mammalian EGRs can be determined by inspecting their amino acid sequences and comparing them with the domains just described.

Recent studies (Gashler et al., *Molec. Cell. Biol.*, 13:4556 (1993)) identified a small region on the 5' side of the zinc finger-encoding sequence of Egr-1 corresponding to amino acids 281–314, FIG. 2 [SEQ ID NO:2], called the "repression domain." The "repression domain" imparts a negative influence on certain biochemical activities of Egr-1, viz. transactivation of reporter constructs. However, it has been found that the zinc finger domain of mammalian EGR, alone (fragment C of Egr-1, FIG. 1), inhibits the mitogenic activity of PDGF without these negative effects. It has also been found that a fragment of Egr-1 containing the zinc finger domain and the rest of the carboxy-terminal end of the molecule (fragment CD, FIG. 1) has greater inhibitory effect than the zinc finger alone.

Accordingly, in preferred embodiments of this invention the polypeptide fragments and the nucleic acid sequences encoding them have the zinc finger domain of a mammalian EGR, but exclude the "repression domain." A nucleic acid molecule or polypeptide consisting essentially of the zinc finger domain excludes the "repression domain." In another preferred embodiment the invention, the polypeptide fragments and the nucleic acid sequences encoding them consisting essentially of the zinc finger domain and the remainder of the carboxy-terminal end of the molecule.

The methods of this invention employ expression vectors having an expression control sequence operatively linked to a nucleic acid sequence encoding a mammalian EGR, a nucleic acid sequence encoding a fragment of a mammalian EGR comprising the zinc finger domain or a nucleic acid sequence that hybridizes to any of the foregoing nucleic acid sequences under standard hybridization conditions and that encodes a polypeptide having the tumor growth-inhibiting activity of Egr-1. According to one embodiment of the invention, the nucleic acid sequence encodes essentially the zinc finger domain of a mammalian EGR.

As used herein, a nucleic acid molecule "encodes" a polypeptide if transcription of the nucleic acid molecule and translation of the mRNA produce the polypeptide. Thus, nucleic acid molecules of this invention include those whose nucleotide sequence encodes a polypeptide directly, such as cDNA, or whose nucleotide sequence includes introns that are spliced out upon transcription into mRNA, such as genomic DNA. It also includes nucleic acid molecules having sequences which are degenerate versions of any of the aforementioned nucleotide sequences.

As used herein, the term "standard hybridization conditions" refers to salt and temperature conditions substantially equivalent to 5×SSC and 65° C. for both hybridization and wash. The activity of any such DNA sequence can be tested by the assay described in the Example.

The nucleic acid molecules of this invention can be produced by organic synthesis on a commercial nucleic acid synthesizer or through PCR of a nucleic acid encoding a polypeptide useful in this invention. Nucleic acid sequences encoding mammalian EGR can be identified by probing cDNA libraries under standard hybridization conditions with probes derived from mouse Egr-1, human EGR1, human EGR2, human EGR3 or human EGR4 and by analyzing cDNA expression libraries with antibodies against a mammalian EGR. Alternatively, EGR from these mammals can be isolated and partially sequenced, and the sequence can be used to make sets of degenerate nucleic acid probes for probing gene libraries. Other methods for identifying and isolating genes are also known.

The expression vectors of this invention have an expression control sequence operatively linked to a nucleic acid molecule of this invention. An expression control sequence is operatively linked to a nucleic acid molecule when it directs the transcription and translation of that molecule in an appropriate host cell. This includes provision of appropriate start and stop codons.

According to one embodiment of the invention, expression of EGR is constitutive. Expression vectors in which the expression control sequence comprises an RSV or CMV promoter will express EGR constitutively. Both promoters are commonly used in the art for the expression of recombinant nucleic acid molecules. (See, for example, Gorman et al., *Molec. and Cell Biol.*, 2:1044 (1982) and Boshant et al., *Cell*, 41:521 (1985).)

The construction of expression vectors and the expression of genes in transfected cells involves the use of molecular cloning techniques also well known in the art. Sambrook et al., *Molecular Cloning—A Laboratory Manual*, Cold Spring Harbor Laboratory, Cold Spring Harbor, N.Y., (1989) (incorporated herein by reference) provides many protocols in the art of molecular genetics.

Methods of transfecting genes into mammalian cells with expression vectors and obtaining their expression are well known to the art. See, e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990), incorporated herein by reference. Vectors useful in this invention include those capable of transferring genes into mammalian cells. These include viral vectors such as retroviruses, adenoviruses and adeno-associated viruses, plasmid vectors, cosmids, liposomes and the like.

Retroviral vectors are useful for treating tumors involving PDGF-induction of mitogenesis by gene therapy. In one embodiment of this invention, the retroviral packaging cell line such as PA317 (American Type Culture Collection, Bethedsa, Md., accession number CRL 9078) is used to create infective amphotrophic retroviral vectors. The retroviral plasmid, pLNCX (D. Miller and G. Rosman, *Biotechniques*, 7:980 (1989)) can contain the expression control sequence operatively linked to the nucleic acid sequence to be expressed. That plasmid contains a Maloney murine leukemia virus LTR promoter/enhancer (L); neomycin resistance gene encoding neomycin phosphotransferase (N); a human cytomegalic virus LTR/enhancer (C) and the coding gene to be expressed (X). The gene is inserted by standard techniques at a pre-existing cloning site by replacement of the phosphotransferase gene for neomycin resistance for one encoding a phosphotransferase of hygromycin resistance. Retroviruses such as pLHCC (pLHCX in which X is the C domain of Egr-1) or pLHCCD (pLHCX in which X is the CD domain of Egr-1) can be used directly to treat tumors. Alternatively, tumors can be treated with irradiated packaging cells which express these retroviruses.

Experiments, described below, were performed to investigate the mechanism of Egr-1 regulation of v-sis action. In these experiments NIH3T3 cells were transformed by the v-sis gene under the control of a metallothionine (MT-I)

promoter. Results showed that Egr-1 does not regulate the activity of the MT-I promoter. While not wishing to be bound by theory, it believed that EGR inhibits the mitogenic activity of PDGF by regulating transcription of genes induced as a result of signal transduction following the binding of PDGF to the receptor tyrosine kinase.

Other oncogenes are known that also act by the binding of their gene products to the receptor tyrosine kinase. These molecules, said to belong to the receptor tyrosine kinase ("RTK") ligand group, include, without limitation, Epidermal Growth Factor (EGF), Nerve Growth Factor (NGF) and Fibroblast Growth Factor (FGF). Upon activation by their respective ligands, RTK's become active tyrosine kinases, binding and phosphorylating cellular proteins. Phosphorylation activates these proteins which, in turn, activates protein kinase-C activation, and activation of c-Ras GTPase activity, which both have mitogenic activity.

Since the mitogenic activity of RTK ligands, including PDGF appear to function by the same mechanism, it is expected that constitutive expression of EGR also inhibits the growth of cells induced by the mitogenic activity of growth factors of the RTK ligand group. Accordingly, this invention provides methods useful for inhibiting the growth of a tumor cell in an individual or a transformed culture cell induced by the mitogenic activity of a RTK ligand.

The methods involve transfecting the cell with an expression vector comprising an expression control sequence operatively linked to a nucleic acid sequence encoding a mammalian RTK ligand, a nucleic acid sequence encoding a fragment of a mammalian RTK ligand comprising the three zinc fingers or a nucleic acid sequence that hybridizes to any of the foregoing nucleic acid sequences under standard hybridization conditions and that encodes a polypeptide that inhibits the mitogenic activity of PDGF.

The following Example is intended to illustrate but not limit the invention.

EXAMPLE

NIH3T3 cells (ATCC accession number CRL-1658) and clone SN30-14, that expresses v-sis conditionally, were maintained in Dulbecco's modified Eagle's medium (DMEM) (Irvine Scientific, Irvine, Calif.) containing 5% calf serum or 5% fetal bovine serum, respectively, at 37° C. in 5% $CO_2$. Cells ($5 \times 10^5$ or $2 \times 10^5$ for 100 and 60 mm dishes (Falcon), respectively) were transfected by the standard calcium phosphate method with 20 or 10 µg DNA, respectively, of different combinations of plasmids as indicated. The total amount of DNA transfected was equalized by including insert-free vector plasmids. Forty hours after transfection, the cultures were trypsinized (Irvine Scientific) and reseeded at 1:4 ratio for selection with G418 (Gibco-BRL, Bethesda, Md.) at 400 mg/ml. Two weeks to 21 days later, the cells were fixed and stained with Giemsa dye (Fluka Biochemicals). The foci in each half or quadrant were counted and statistically analyzed by the student's two-tailed t-test. The results were analyzed by a software program from Systat (Evanston, Ill.).

Expression vectors encoding full length (2.1 kb) Egr-1 and antisense Egr-1 (Rge) were constructed replacing the RSV in RSV-Egr-1 (Madden et al., supra) with the CMV LTR. This was to maximize expression and to match it with the CMV-WT1 vector. Both Egr-1 expression vectors were tested for level of expression with no significant difference observed and so they were used interchangeably.

To characterize the products of in vitro translation, about 1 to 2 µg of RNA template was translated in a rabbit reticulocyte lysate (25 µl) in the presence of [35S]-methionine according to the manufacturer's protocols (Promega).

For the experiment, equimolar amounts of each protein were added by including a small amount of 35S-cysteine in the protein synthesis step. We then determined the concentration of protein made from the radioactivity and the calculated number of cysteines in the molecule.

These studies were made on NIH3T3 cells. The expression of transfected plasmids is denoted by E for Egr-1; W for WT-1 (Wilm's tumor gene); R for antisense Egr-1; A, B, C, D, for the domains of Egr-1 (see diagram in FIG. 1). The expression of these genes was directed by the CMV or RSV promoters. To select for expression, the bacterial gene for neomycin resistance, n, was introduced by pSV2neo by cotransfection.

In some studies, to transform NIH3T3 cells, the expression vector pMTsis (Mercola et al., Oncogene, 7:1793 (1992)) was co-transfected. Where indicated, the cloned line SN30-14 was used in place of NIH3T3 since this NIH3T3-based line expresses v-sis constitutively and inducibly by the addition of heavy metal salts to the culture medium (Mercola et al., 1992, supra). In these cases, the plasmid pHygro was used to select for cells expressing the transfected vectors by their resistance to the antibiotic, hygromycin.

In order to test the effect of excess Egr-1 expression on the growth of normally cycling NIH3T3 cells monolayers of cells were transfected with pCMV-Egr-1 or with antisense Egr (pCMV-Rge) together with pSV2neo to determine if these vectors affect growth or colony formation. Four weeks after selection with G418, there were no significant differences between the number of colonies in the presence or absence of pCMV-Egr-1 or pCMV-Rge. In contrast, the addition of v-sis to NIH3T3 in transfection studies increased the number of foci by 8-fold. The size and number of foci in v-sis expressing cells was modest compared to those obtained with activated c-Ha-Ras (included as a positive control for transfection efficiency, see below) but was suitable range to determine if the number of foci could be modulated by Egr-1 or Rge expression.

Expression plasmids encoding activated ras (Leu 61) and mutant Ras (Asn 17) (Feig and Cooper, Mol. Cell. Biol., 8:3235 (1988)) inserted into pZIPneoSV(X) (Cai et al., Mol. Cell. Biol., 10:5314–5323 (1990); Land et al., Mol. Cell. Biol., 6:1917 (1986)) were used. CMV-WT1 (Madden et al., supra) was also used, pMTsis and the antisense version sas were described earlier (Mercola et al., In Osteosarcoma Conference Proceedings, 375–386 (1993); Mercola et al., 1992, supra). The mouse metallothionine promoter in this plasmid is truncated and contains metal responsive elements but not steroid responsive elements.

The plasmid pMTsis (Mercola et al., 1992, supra) was cotransfected by mixing with the DNA of either pCMV-Egr-1, pCMV-Rge or pCMV-WT1 together with pSV2neo in order to select for NIH3T3 cells that became resistant to G418. The ability of the cells to form colonies was evident in 14 to 20 days. The numbers of colonies were evaluated after fixing and staining: statistical analysis was performed using the two-tailed student's t-test. For pMTsis transfected cells, the number of colonies was moderately high and this was reduced to 68% by the Egr-1 expression vector. The effect of Egr-1 was dose-dependent for the two higher doses of Egr-1. WT1 was also inhibitory to focus formation (17% of colony frequency compared to v-sis alone). Moreover, when vectors for Egr-1 were replaced by a vector for expression of the antisense version of Egr-1 the number of foci increased to 149%. This result confirmed that the observation was specific to Egr-1 expression. The focus-forming frequencies evaluated in this experiment were statistically significantly different for each case described here (p=0.03 to 0.001). This study was repeated at least three times with similar results.

We next tested the ability of the cells to grow in soft agar as a more stringent assay for the transformed state. For soft agar assays described herein, 10 days after selection of transfected cells with G418, each sample was trypsinized and the cells seeded at $2\times10^5$ into each of four 60 mm plates in medium containing 0.26% agar layered over a 0.65% agar medium. The plates were incubated at 37° C. in a humidified atmosphere of 5% $CO_2$, fed every 3 days with fresh liquid medium and examined microscopically for the presence of colonies 14–20 days after seeding. Colonies were stained with p-iodotetrazolium violet overnight before counting.

As in the experiment described above, similar combinations of expression vectors were cotransfected into NIH3T3 cells and cultures were selected for neomycin resistance over 10 days with G418. Cells were cultured for a further 2 to 4 weeks in soft agar. V-sis-expressing NIH3T3 cells formed a basal level of colonies. There were fewer and smaller colonies in pCMV-Egr-1 transfected cells, while the colonies of cells that contained the antisense Egr-1 vector were larger and more numerous. Enumeration of the colonies produced by cells that were transfected with Egr-1, Rge, or WT1 expression plasmids was performed.

Colonies above a certain size were counted; this evaluation does not take into account the fact that the average size of the colonies differed in each cell type. The results were very similar to those for the focus-forming assay, that is, Egr-1 and WT1 expression were inhibitory (41% [p=0.003] and 64% [p=0.003] of control, respectively) while Rge was stimulatory (126%, p=0.03) to transformed growth. Overexpression of Egr-1 in v-sis transformed NIH3T3 cells decreases the transforming capability to the basal level exhibited by control NIH3T3 cells. This experiment was repeated at least three times with similar qualitative results but somewhat variable quantitative results between experiments. Variation probably depended on the efficiency of the transfection since it occurred with different DNA preparations and different batches of cells.

The variability of transfection efficiency was of concern and two strategies were employed to control for this. One was to repeat each experiment many times, and the other was to use positive and negative controls to check for transfection efficiency. For instance, transformation depended on the expression of v-sis, since SN30-14 cells transfected with the antisense sis expression vector, pMTsas, completely abrogated the ability of the cells to grow in soft agar. In contrast, an activated Ras vector rapidly grew large diffuse agar colonies while very few small colonies were produced by transfection with a mutant Ras vector wherein codon 17 is changed to asparagine (Feig and Cooper, supra).

The morphology of cells containing the antisense Egr-1-expressing plasmid was quite distinct from parental NIH3T3 or SN30-14 cells. A soft agar colony of NSR cells was removed, trypsinized and seeded in a tissue-culture dish and passaged several times. The spindle-shaped, highly-refractile cells grew in foci and networks: an appearance associated with transformation. This appearance persisted for at least ten divisions and repeated soft agar growth tests showed that this clone grew rapidly into large colonies of cells. In contrast, cultures derived from the small agar colonies that over-expressed Egr-1, even in the presence of the antisense-expressing (Rge) vector (NSER cells), grew as flattened cells much like normal NIH3T3 cells. Thus the observations are entirely consistent for the two different assays and strongly argue that inclusion of the pCMV-Egr-1 vector suppresses transformation and conversely that the inclusion of pCMV-Rge augments transformation. The stability of Rge expression in SN30-14 eventually declined with extended passage. This was obvious, however, as the cells would then appear flatter in monolayer culture.

Cells growing in vitro may behave differently in the whole animal when unknown regulatory activities may prevail. Cells cloned from soft agar colonies were tested for their ability to grow as tumors in nu/nu mice.

Cells (usually $5\times10^5$) were injected into two subcutaneous sites on the shoulders of Balbc nu/nu mice. Animals were inspected at regular intervals for the appearance of visible tumors to measure the time of first appearance. After sacrifice of the mice, the tumors were weighed and their growth rates measured as mg/day. The results were statistically analyzed as above.

The tumorigenicity of cells expressing v-sis was decreased by the activity of Egr-1 and increased in cells transfected with Rge compared to NIH3T3 cells and parental SN30-14 cells. In one experiment, the growth rate of tumors for SN30-14 cells expressing Egr-1 was significantly reduced ($p<0.05$) compared to SN30-14 cells, while for Rge-expressing cells the rate was on average higher but not significantly so. In another experiment, Egr-1 suppressed tumor growth by 30% while antisense Egr-1 expression gave a rate of tumor formation 2.1-fold faster than untransfected SN30-14 cells. In addition, tumors started to appear by day 12 in NSR cells and grew at an average of 44.7 mg/day while only 3 of 13 Egr-expressing cells gave palpable tumors by day 21. Two of 6 mice had no tumors 35 days after injection with Egr-expressing cells.

Figure 6A:
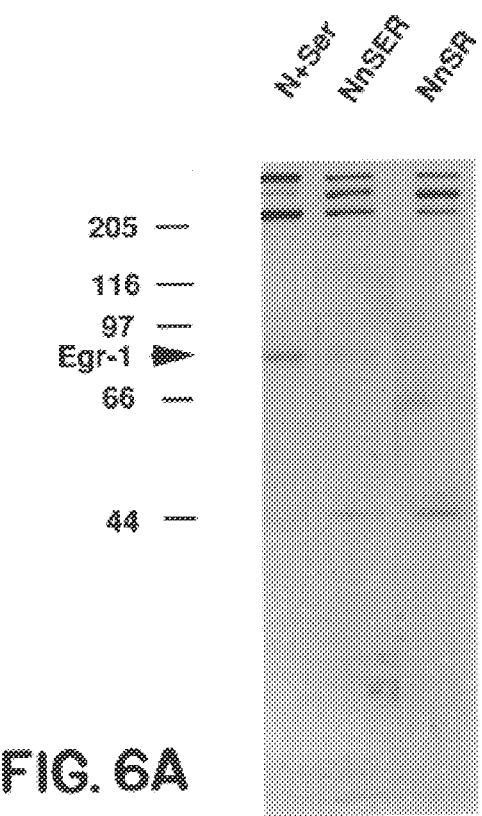
FIGS. 6A to 6D depict gels estimating the amount of Egr-1 protein present in NIH3T3 clones.

Three types of measurements were made to determine the level of constitutive expression of Egr-1 in transfected cells. First, cells growing in logarithmic phase were compared after metabolic labeling with [35S]methionine with NIH3T3 cells treated for 1 hour with serum. Egr-1 in cell lysates was immunoprecipitated, electrophoretically separated and analyzed by autofluorography. FIG. 6A shows that there was a low level of Egr-1 in NIH3T3 cells that were transfected with pMTsis and pCMV-Egr-1 and little or none in those expressing sis and Rge (compare lanes 2 and 3). However, in serum-stimulated NIH3T3 cells, there was a readily detectable level of Egr-1 (lane 1).

Immunoprecipitation was performed as described earlier (Edwards et al., Dev. Biol., 148:165 (1991)). Cells were metabolically-labeled by incubation of cells for 60 minutes with 400 $\mu$ci/ml [35S]-methionine and cysteine (ICN) in cysteine and methionine-free medium. The washed and lysed cells were immunoprecipitated with rabbit anti-Egr-1 or with rabbit anti-v-sis antisera (Mercola et al., 1992, supra). The antigen-antibody complexes were analyzed on 7.5% SDS-PAGE gels in reducing sample buffer.

There was a low level of Egr-1 in NIH3T3 cells that were transfected with pMTsis and pCMV-Egr-1 and little or none in those expressing sis and Rge (compare lanes 2 and 3). However, in serum-stimulated NIH3T3 cells, there was a readily detectable level of Egr-1 (lane 1).

Figure 6B:
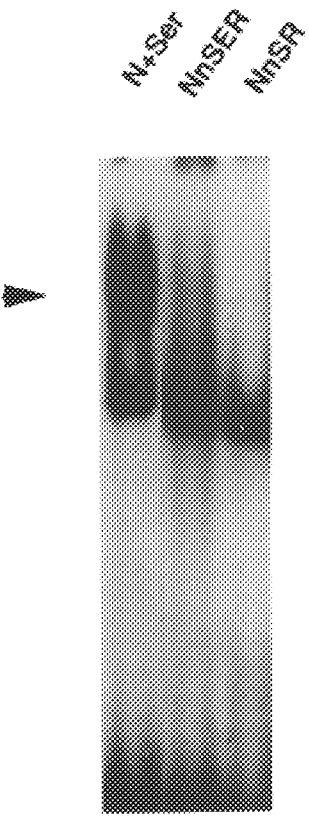

Second, the ability of Egr-1 in nuclear extracts to bind to and retard the electrophoretic migration of the GCE-containing [32P]oligonucleotide (the Egr-1 binding site) was examined. The gel retardation procedure was essentially as described in Huang and Adamson, *DNA and Cell. Biol.*, 12:265–273 (1993). The method developed by Dignam et al., *Nucl. Acids Res.*, 11:1475–1489 (1983) was applied to prepare nuclear extracts. Ten μg nuclear protein extract was incubated with 1 ng of [32P]-g-ATP end-labeled oligonucleotide (5'-GATCTCGCG GGGGCGAGGG GGATC-3' [SEQ ID NO:12]) for 20 minutes at room temperature in the buffer containing 20 mM HEPES (pH 7.5), 12% glycerol, 70 mM KCl, 5 mM $MgCl_2$, 1 mg/ml BSA, 1 mg/dI-dC, 0.25 mg/ml sonicated herring sperm DNA, with the addition of 1 mM DTT and 100 μM $ZnCl_2$. The product was analyzed on a 5% polyacrylamide gel in 0.5×Tris-borate-EDTA buffer at 4° C. FIG. 6B shows that the amount of oligonucleotide retardation was in proportion to the level of Egr-1 synthesis for the same cells as in lanes 1, 2 and 3 in FIG. 6A.

Third, the total Egr-1 protein present in lysates of NIH3T3 cells stably-expressing pMTsis (clone SN30-14, Mercola et al., 1992, supra) was compared in immunoblotting (Western blot) studies with antisense-containing cells. Western blotting was carried out as follows. Cells grown to near-confluence were harvested and dissolved by the addition of SDS-containing lysis buffer. Lysate volumes containing $1.5 \times 10^5$ cells were used for sodium dodecyl sulfate (SDS)-polyacrylamide gel electrophoresis on a 7.5% gel in the presence of 2-mercaptoethanol. Proteins were electrophoretically transferred from the gel to PVDF membrane (Immobilon, Millipore Corp. Orange, Calif.). The transferred membrane was treated with antiserum against Egr-1 protein. The resulting complexes were detected by the ECL system (Amersham Corporation) according to the manufacturer's instructions. Samples from tumors were solubilized in Laemmli sample buffer and equalized for protein loading before SDS-PAGE and immunoblotting as described above.

Figures 6C, 6D:
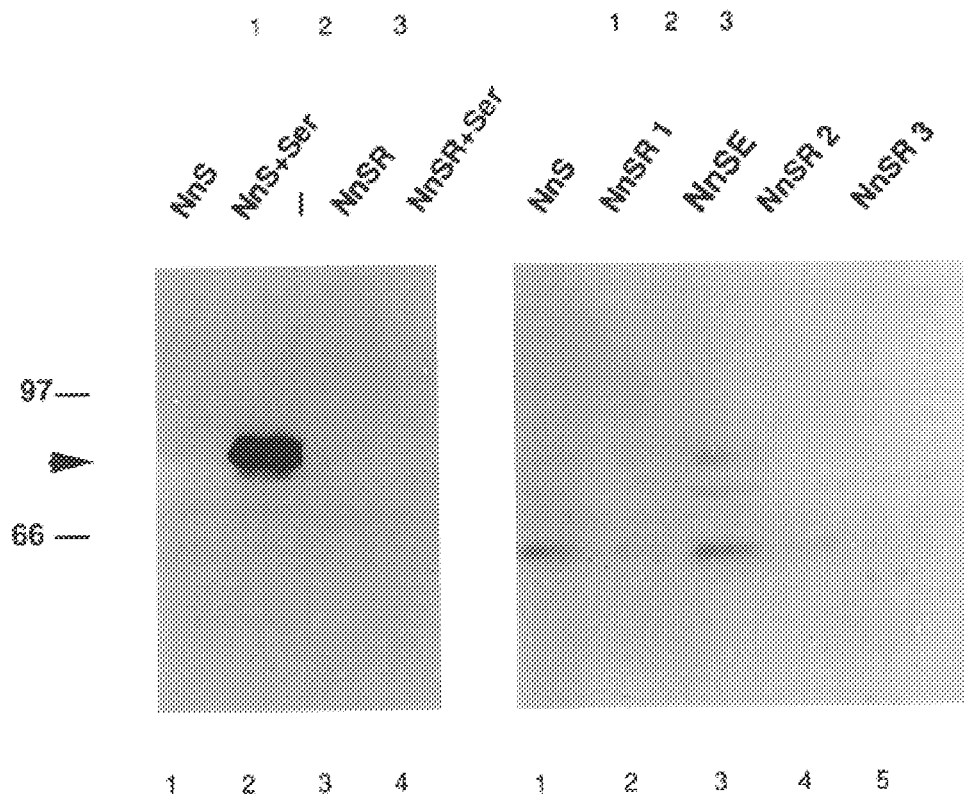

Cells that were cloned from a soft agar growth of SN30-14 cells expressing Rge are the most phenotypically transformed of all the clones that we have isolated. FIG. 6C shows that one of these NnSR clones had no detectable Egr-1 protein even with excessive over-exposure of this Western. In addition, the antisense-expressing cells could not be stimulated to express Egr-1 with serum (FIG. 6C, lane 4), a condition that typically leads to the strong induction of Egr-1 after 50 minutes as shown here (FIG. 6C, lane 2) for exposure of SN30-14 cells. In summary, these measurements demonstrated that sense Egr-1 RNA expression increased, while antisense Egr-1 RNA expression drastically reduced, the basal and induced levels of Egr-1 protein in NIH3T3 cells.

Three of the cell lines that were compared for their rates of tumor formation were analyzed by immunoblotting for constitutive levels of Egr-1 expression in FIG. 6D. The line over-expressing Egr-1 contained 28-fold more Egr-1 protein than SN30-14 cells while there was little or none in all the antisense lines examined (FIG. 6D, lanes 2, 4 and 5). The tumors were also immunoblotted to determine their Egr-1 levels: the results were similar to the levels of Egr-1 in the cells lines before injection. These data confirm that the transfection and selection procedures have the expected effect on Egr-1 levels. Egr-1 expression does not suppress the activity of the MT-I promoter.

A simple explanation for the suppressive effect of the expression of Egr-1 in SN30-14 cells is that the mouse MT-I promoter activity is inhibited by Egr-1 and this reduces v-sis expression. When v-sis expression is induced in SN30-14 cells by the addition of 50 μM Zn acetate to the culture medium, a simultaneous induction of Egr-1 occurs. In a representative experiment v-sis and Egr-1 syntheses were measured by immunoprecipitation from 35S-labeled cell lysates over 4 hours after Zn+2 addition. In addition, Egr-1 protein levels measured by immunoblotting gave a similar result for the steady-state levels of Egr-1 protein. This argues against a simple inhibition of the MT-I promoter by Egr-1.

As the initial step to studying the mechanism of the biological activity described above as well as the relationship between structure and function of the Egr-1 protein, a series of truncated forms of Egr-1 were constructed using standard recombinant DNA manipulation. The component parts are summarized in FIG. 1. "A" domain consists of the first of the two exons that make up Egr-1 and "C" has the zinc-finger domain that is responsible for binding to the GC-rich Egr element (GCE) in DNA. "B" domain lies between "A" and "C," while "D" domain is the remainder of the protein.

The plasmids were constructed as follows. First, pGEM-4-Egr-1 was constructed by inserting the DNA encoding Egr-1 into the polylinker site of pGEM. (Madden et al., supra.) For pG-AB, plasmid pGEM-4-Egr-1 was cut with Sph 1 and ligated with an Xba 1 linker to introduce a stop codon into the vector. For pG-ABC, plasmid OC 3.1 full-length Egr-1 cDNA was digested with BglI and the protruding 3' terminus was removed by T4 DNA polymerase. The resulting fragment was inserted into pGEM 1 and the Xba 1 linker was used to create a stop codon. To construct plasmid pG-CD, the fragment in plasmid OC 3.1 corresponding to Egr-1 cDNA bp1 to 304 was released by double digestion with Eco RI and Pst I and was inserted into pGEM 1 creating pG-Egr-1-5'. pG-Egr-1 5' was then digested with Pst I and the terminus so formed was blunted by treatment with the Klenow fragment and ligated with the Rsa I fragment extending from bp 1226 to 2258 in the Egr-1 cDNA sequence [SEQ ID NO:1]. To make plasmid pG-C, the fragment recovered from pG-CD after digestion with Bgl 1 and blunting with T4 DNA polymerase was subcloned into the pGEM 1 after digestion with Sma 1. To make a stop codon, the resultant plasmid was treated with Bam H1 and then blunted at the Bam H1 terminus by the Klenow fragment. For plasmid pG-D, the sequence containing Egr-1 cDNA [SEQ ID NO:1] from bp 73 (5') to 303 (3') and from bp 1551 (5') to 2258 (3') obtained by Bgl I digestion of pG-CD was inserted into the intermediate vector pG-Egr 1 5' after Pst I digestion, blunting and Hind III digestion. Plasmid Bluescript-Egr-1, (BS Egr-1) contained the entire Egr-1 cDNA sequence cloned into the Eco R1 site of Bluescript (Stratagene).

The same Egr-1 fragments were cloned into pRSV-Erg-1, replacing the Egr-1 coding sequence to generate A, AB, ABC, C and CD polypeptides after transfection into SN30-14 cells.

pG-ABC, pG-CD, pG-C and pG-D were linearized with Hind III and transcribed into mRNA by using T7 RNA. After linearization of BS Egr-1 by Bam I and pG-AB by Hind III the transcripts of Egr-1 and AB domain were generated using T3 RNA polymerase and Sp6 RNA polymerase, respectively.

Various combinations of the domains were cloned into pGEM-1 vectors that were then used to synthesize the mRNA and the protein in a reticulocyte lysate system. The resulting lysates were analyzed by SDS-PAGE. The apparent MWs do not correspond to the calculated ones; a similar situation occurs with the full length Egr-1 protein which migrates at a rate that gives an apparent MW of 80 kDa. To confirm that these constructions are the predicted Egr-1 fragments, the lysates were immunoprecipitated with a rabbit polyclonal antibody raised to the whole protein purified from extracts of a baculovirus expression system (Ragona et al., *DNA and Cell Biol.,* 10:61 (1991)). Results confirmed that the antibody recognizes all fragments and that immunoprecipitates migrate in the expected position relative to each other.

The ability of the domains of Egr-1 to bind to a synthetic GCE was tested in gel shift assays. Egr-1, ABC, CD, and C domains could bind to GCE but AB and D domains could not. The binding was specific since antibody against Egr-1 could completely block the binding activity, but non-immune serum had no effect on DNA binding activity. This result indicated that the C domain contained all the information necessary for DNA binding activity.

When the experiment was repeated in the presence of equimolar amounts of each binding domain, we found that the CD domain had the highest binding activity, followed by C, ABC and Egr-1. The ratios of the binding activity of the domains compared with Egr-1 were 4.9, 7.9 and 2.4, respectively for C, CD and ABC.

The fragments of Egr-1 cDNA described above were also cloned into eukaryotic expression vectors at a position downstream of the strong promoter derived from the Rous sarcoma virus (RSV), but all other features were the same as described above for the in vitro transcription and translation. The expression of the ABC fragment was confirmed by immunoblotting and the ABC protein was confirmed in cells transfected with pRSV-ABC. These eukaryotic expression vectors were then tested in the focus-forming assays after transfection into NIH3T3 cells as before. We found that all the fragments containing the C (DNA-binding) domain were able to reduce the number of v-sis-induced foci. Fragment D, in contrast, had little effect, presumably because it does not contain the GCE-binding site. It is interesting that fragment CD is more inhibitory than C ($p=0.05$), and this correlates with the higher GCE binding activity of CD compared with C. Again the combined effect of Egr-1 and fragment C was significantly more repressive than their separate effects. These foci were characterized by large size and ring-like colonies in NnSR cells that expressed antisense Egr-1. Ring structures were seen when the colonies become large piles of cells that fall off during the washing and fixing process.

We also tested some combinations of expression plasmids in soft agar growth assays with similar results. The CD and ABC fragments were able to reduce colony growth significantly but AB was not. We concluded that the DNA-binding domain was a necessary feature for the ability of Egr-1 to suppress transformed growth in this system.

Although the invention has been described with reference to the presently-preferred embodiments, it should be understood that various modifications can be made without departing from the spirit of the invention. Accordingly, the invention is limited only by the claims that follow.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 3068 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 370..1858

( x i ) SEQUENCE DESCRIPTION: SEQ ID NO:1:

```
GGGGAGCCGC  CGCCGCGATT  CGCCGCCGCC  GCCAGCTTCC  GCCGCCGCAA  GATCGGCCCC        60

TGCCCCAGCC  TCCGCGGCAG  CCCTGCGTCC  ACCACGGGCC  GCGGCTACCG  CCAGCCTGGG       120

GGCCCACCTA  CACTCCCCGC  AGTGTGCCCC  TGCACCCCGC  ATGTAACCCG  GCCAACCCCC       180

GGCGAGTGTG  CCCTCAGTAG  CTTCGGCCCC  GGGCTGCGCC  CACCACCCAA  CATCAGTTCT       240

CCAGCTCGCT  GGTCCGGGAT  GGCAGCGGCC  AAGGCCGAGA  TGCAATTGAT  GTCTCCGCTG       300

CAGATCTCTG  ACCCGTTCGG  CTCCTTTCCT  CACTCACCCA  CCATGGACAA  CTACCCCAAA       360

CTGGAGGAG  ATG  ATG  CTG  CTG  AGC  AAC  GGG  GCT  CCC  CAG  TTC  CTC  GGT       408
            Met  Met  Leu  Leu  Ser  Asn  Gly  Ala  Pro  Gln  Phe  Leu  Gly
             1              5                        10

GCT  GCC  GGA  ACC  CCA  GAG  GGC  AGC  GGC  GGT  AAT  AGC  AGC  AGC  AGC  ACC     456
Ala  Ala  Gly  Thr  Pro  Glu  Gly  Ser  Gly  Gly  Asn  Ser  Ser  Ser  Ser  Thr
 15                        20                         25

AGC  AGC  GGG  GGC  GGT  GGT  GGG  GGC  GGC  AGC  AAC  AGC  GGC  AGC  GCC     504
Ser  Ser  Gly  Gly  Gly  Gly  Gly  Gly  Gly  Ser  Asn  Ser  Gly  Ser  Ser  Ala
 30                        35                         40                         45
```

```
TTC AAT CCT CAA GGG GAG CCG AGC GAA CAA CCC TAT GAG CAC CTG ACC         552
Phe Asn Pro Gln Gly Glu Pro Ser Glu Gln Pro Tyr Glu His Leu Thr
            50                  55                  60

ACA GAG TCC TTT TCT GAC ATC GCT CTG AAT AAT GAG AAG GCG ATG GTG         600
Thr Glu Ser Phe Ser Asp Ile Ala Leu Asn Asn Glu Lys Ala Met Val
        65                  70                  75

GAG ACG AGT TAT CCC AGC CAA ACG ACT CGG TTG CCT CCC ATC ACC TAT         648
Glu Thr Ser Tyr Pro Ser Gln Thr Thr Arg Leu Pro Pro Ile Thr Tyr
            80                  85                  90

ACT GGC CGC TTC TCC CTG GAG CCC GCA CCC AAC AGT GGC AAC ACT TTG         696
Thr Gly Arg Phe Ser Leu Glu Pro Ala Pro Asn Ser Gly Asn Thr Leu
        95                 100                 105

TGG CCT GAA CCC CTT TTC AGC CTA GTC AGT GGC CTC GTG AGC ATG ACC         744
Trp Pro Glu Pro Leu Phe Ser Leu Val Ser Gly Leu Val Ser Met Thr
110                 115                 120                 125

AAT CCT CCG ACC TCT TCA TCC TCG GCG CCT TCT CCA GCT GCT TCA TCG         792
Asn Pro Pro Thr Ser Ser Ser Ser Ala Pro Ser Pro Ala Ala Ser Ser
            130                 135                 140

TCT TCC TCT GCC TCC CAG AGC CCG CCC CTG AGC TGT GCC GTG CCG TCC         840
Ser Ser Ser Ala Ser Gln Ser Pro Pro Leu Ser Cys Ala Val Pro Ser
        145                 150                 155

AAC GAC AGC AGT CCC ATC TAC TCG GCT GCG CCC ACC TTT CCT ACT CCC         888
Asn Asp Ser Ser Pro Ile Tyr Ser Ala Ala Pro Thr Phe Pro Thr Pro
            160                 165                 170

AAC ACT GAC ATT TTT CCT GAG CCC CAA AGC CAG GCC TTT CCT GGC TCG         936
Asn Thr Asp Ile Phe Pro Glu Pro Gln Ser Gln Ala Phe Pro Gly Ser
        175                 180                 185

GCA GGC ACA GCC TTG CAG TAC CCG CCT CCT GCC TAC CCT GCC ACC AAA         984
Ala Gly Thr Ala Leu Gln Tyr Pro Pro Pro Ala Tyr Pro Ala Thr Lys
190                 195                 200                 205

GGT GGT TTC CAG GTT CCC ATG ATC CCT GAC TAT CTG TTT CCA CAA CAA        1032
Gly Gly Phe Gln Val Pro Met Ile Pro Asp Tyr Leu Phe Pro Gln Gln
            210                 215                 220

CAG GGA GAC CTG AGC CTG GGC ACC CCA GAC CAG AAG CCC TTC CAG GGT        1080
Gln Gly Asp Leu Ser Leu Gly Thr Pro Asp Gln Lys Pro Phe Gln Gly
        225                 230                 235

CTG GAG AAC CGT ACC CAG CAG CCT TCG CTC ACT CCA CTA TCC ACT ATT        1128
Leu Glu Asn Arg Thr Gln Gln Pro Ser Leu Thr Pro Leu Ser Thr Ile
            240                 245                 250

AAA GCC TTC GCC ACT CAG TCG GGC TCC CAG GAC TTA AAG GCT CTT AAT        1176
Lys Ala Phe Ala Thr Gln Ser Gly Ser Gln Asp Leu Lys Ala Leu Asn
        255                 260                 265

ACC ACC TAC CAA TCC CAG CTC ATC AAA CCC AGC CGC ATG CGC AAG TAC        1224
Thr Thr Tyr Gln Ser Gln Leu Ile Lys Pro Ser Arg Met Arg Lys Tyr
270                 275                 280                 285

CCC AAC CGG CCC AGC AAG ACA CCC CCC CAT GAA CGC CCA TAT GCT TGC        1272
Pro Asn Arg Pro Ser Lys Thr Pro Pro His Glu Arg Pro Tyr Ala Cys
            290                 295                 300

CCT GTC GAG TCC TGC GAT CGC CGC TTT TCT CGC TCG GAT GAG CTT ACC        1320
Pro Val Glu Ser Cys Asp Arg Arg Phe Ser Arg Ser Asp Glu Leu Thr
        305                 310                 315

CGC CAT ATC CGC ATC CAC ACA GGC CAG AAG CCC TTC CAG TGT CGA ATC        1368
Arg His Ile Arg Ile His Thr Gly Gln Lys Pro Phe Gln Cys Arg Ile
            320                 325                 330

TGC ATG CGT AAC TTC AGT CGT AGT GAC CAC CTT ACC ACC CAC ATC CGC        1416
Cys Met Arg Asn Phe Ser Arg Ser Asp His Leu Thr Thr His Ile Arg
        335                 340                 345

ACC CAC ACA GGC GAG AAG CCT TTT GCC TGT GAC ATT TGT GGG AGG AAG        1464
Thr His Thr Gly Glu Lys Pro Phe Ala Cys Asp Ile Cys Gly Arg Lys
350                 355                 360                 365
```

| | | | | | | | | | | | | | | | | |
|---|---|---|---|---|---|---|---|---|---|---|---|---|---|---|---|---|
| TTT | GCC | AGG | AGT | GAT | GAA | CGC | AAG | AGG | CAT | ACC | AAA | ATC | CAT | TTA | AGA | 1512 |
| Phe | Ala | Arg | Ser | Asp | Glu | Arg | Lys | Arg | His | Thr | Lys | Ile | His | Leu | Arg | |
| | | | 370 | | | | | 375 | | | | | 380 | | | |
| CAG | AAG | GAC | AAG | AAA | GCA | GAC | AAA | AGT | GTG | GTG | GCC | TCC | CCG | GCT | GCC | 1560 |
| Gln | Lys | Asp | Lys | Lys | Ala | Asp | Lys | Ser | Val | Val | Ala | Ser | Pro | Ala | Ala | |
| | | | 385 | | | | | 390 | | | | | 395 | | | |
| TCT | TCA | CTC | TCT | TCT | TAC | CCA | TCC | CCA | GTG | GCT | ACC | TCC | TAC | CCA | TCC | 1608 |
| Ser | Ser | Leu | Ser | Ser | Tyr | Pro | Ser | Pro | Val | Ala | Thr | Ser | Tyr | Pro | Ser | |
| | | | 400 | | | | | 405 | | | | | 410 | | | |
| CCT | GCC | ACC | ACC | TCA | TTC | CCA | TCC | CCT | GTG | CCC | ACT | TCC | TAC | TCC | TCT | 1656 |
| Pro | Ala | Thr | Thr | Ser | Phe | Pro | Ser | Pro | Val | Pro | Thr | Ser | Tyr | Ser | Ser | |
| | | 415 | | | | | 420 | | | | | 425 | | | | |
| CCT | GGC | TCC | TCC | ACC | TAC | CCA | TCT | CCT | GCG | CAC | AGT | GGC | TTC | CCG | TCG | 1704 |
| Pro | Gly | Ser | Ser | Thr | Tyr | Pro | Ser | Pro | Ala | His | Ser | Gly | Phe | Pro | Ser | |
| 430 | | | | | 435 | | | | | 440 | | | | | 445 | |
| CCG | TCA | GTG | GCC | ACC | ACC | TTT | GCC | TCC | GTT | CCA | CCT | GCT | TTC | CCC | ACC | 1752 |
| Pro | Ser | Val | Ala | Thr | Thr | Phe | Ala | Ser | Val | Pro | Pro | Ala | Phe | Pro | Thr | |
| | | | | 450 | | | | | 455 | | | | | 460 | | |
| CAG | GTC | AGC | AGC | TTC | CCG | TCT | GCG | GGC | GTC | AGC | AGC | TCC | TTC | AGC | ACC | 1800 |
| Gln | Val | Ser | Ser | Phe | Pro | Ser | Ala | Gly | Val | Ser | Ser | Ser | Phe | Ser | Thr | |
| | | | 465 | | | | | 470 | | | | | 475 | | | |
| TCA | ACT | GGT | CTT | TCA | GAC | ATG | ACA | GCG | ACC | TTT | TCT | CCC | AGG | ACA | ATT | 1848 |
| Ser | Thr | Gly | Leu | Ser | Asp | Met | Thr | Ala | Thr | Phe | Ser | Pro | Arg | Thr | Ile | |
| | | 480 | | | | | 485 | | | | | 490 | | | | |
| GAA | ATT | TGC | T | AAAGGGAATA | | AAAGAAAGCA | | AAGGGAGAGG | | CAGGAAAGAC | | | | | | 1898 |
| Glu | Ile | Cys | | | | | | | | | | | | | | |
| | | 495 | | | | | | | | | | | | | | |

| | | | | | |
|---|---|---|---|---|---|
| ATAAAAGCAC | AGGAGGGAAG | AGATGGCCGC | AAGAGGGGCC | ACCTCTTAGG | TCAGATGGAA | 1958 |
| GATCTCAGAG | CCAAGTCCTT | CTACTCACGA | GTAGAAGGAC | CGTTGGCCAA | CAGCCCTTTC | 2018 |
| ACTTACCATC | CCTGCCTCCC | CCGTCCTGTT | CCCTTTGACT | TCAGCTGCCT | GAAACAGCCA | 2078 |
| TGTCCAAGTT | CTTCACCTCT | ATCCAAAGGA | CTTGATTTGC | ATGGTATTGG | ATAAATCATT | 2138 |
| TCAGTATCCT | CTCCATCACA | TGCCTGGCCC | TTGCTCCCTT | CAGCGCTAGA | CCATCAAGTT | 2198 |
| GGCATAAAGA | AAAAAAAATG | GGTTTGGGCC | CTCAGAACCC | TGCCCTGCAT | CTTTGTACAG | 2258 |
| CATCTGTGCC | ATGGATTTTG | TTTTCCTTGG | GGTATTCTTG | ATGTGAAGAT | AATTTGCATA | 2318 |
| CTCTATTGTA | TTATTTGGAG | TTAAATCCTC | ACTTTGGGGG | AGGGGGGAGC | AAAGCCAAGC | 2378 |
| AAACCAATGA | TGATCCTCTA | TTTTGTGATG | ACTCTGCTGT | GACATTAGGT | TTGAAGCATT | 2438 |
| TTTTTTTTCA | AGCAGCAGTC | CTAGGTATTA | ACTGGAGCAT | GTGTCAGAGT | GTTGTTCCGT | 2498 |
| TAATTTTGTA | AATACTGGCT | CGACTGTAAC | TCTCACATGT | GACAAAGTAT | GGTTTGTTTG | 2558 |
| GTTGGGTTTT | GTTTTTGAGA | ATTTTTTTGC | CCGTCCCTTT | GGTTTCAAAA | GTTTCACGTC | 2618 |
| TTGGTGCCTT | TTGTGTGACA | CGCCTTCCGA | TGGCTTGACA | TGCGCAGATG | TGAGGGACAC | 2678 |
| GCTCACCTTA | GCCTTAAGGG | GGTAGGAGTG | ATGTGTTGGG | GGAGGCTTGA | GAGCAAAAAC | 2738 |
| GAGGAAGAGG | GCTGAGCTGA | GCTTTCGGTC | TCCAGAATGT | AAGAAGAAAA | AATTTAAACA | 2798 |
| AAAATCTGAA | CTCTCAAAAG | TCTATTTTTC | TAAACTGAAA | ATGTAAATTT | ATACATCTAT | 2858 |
| TCAGGAGTTG | GAGTGTTGTG | GTTACCTACT | GAGTAGGCTG | CAGTTTTTGT | ATGTTATGAA | 2918 |
| CATGAAGTTC | ATTATTTTGT | GGTTTTATTT | TACTTTGTAC | TTGTGTTTGC | TTAAACAAAG | 2978 |
| TAACCTGTTT | GGCTTATAAA | CACATTGAAT | GCGCTCTATT | GCCCATGGGA | TATGTGGTGT | 3038 |
| GTATCCTTCA | GAAAATTAA | AAGGAAAAAT | | | | 3068 |

( 2 ) INFORMATION FOR SEQ ID NO:2:

(i) SEQUENCE CHARACTERISTICS:
   (A) LENGTH: 496 amino acids
   (B) TYPE: amino acid
   (D) TOPOLOGY: linear (ii) MOLECULE TYPE: protein (xi) SEQUENCE DESCRIPTION: SEQ ID NO:2:

```
Met Met Leu Leu Ser Asn Gly Ala Pro Gln Phe Leu Gly Ala Ala Gly
 1               5                  10                  15

Thr Pro Glu Gly Ser Gly Gly Asn Ser Ser Ser Thr Ser Ser Gly
             20                  25                  30

Gly Gly Gly Gly Gly Gly Ser Asn Ser Gly Ser Ser Ala Phe Asn Pro
             35                  40                  45

Gln Gly Glu Pro Ser Glu Gln Pro Tyr Glu His Leu Thr Thr Glu Ser
        50                  55                  60

Phe Ser Asp Ile Ala Leu Asn Asn Glu Lys Ala Met Val Glu Thr Ser
 65                  70                  75                  80

Tyr Pro Ser Gln Thr Thr Arg Leu Pro Pro Ile Thr Tyr Thr Gly Arg
                     85                  90                  95

Phe Ser Leu Glu Pro Ala Pro Asn Ser Gly Asn Thr Leu Trp Pro Glu
                100                 105                 110

Pro Leu Phe Ser Leu Val Ser Gly Leu Val Ser Met Thr Asn Pro Pro
            115                 120                 125

Thr Ser Ser Ser Ser Ala Pro Ser Pro Ala Ala Ser Ser Ser Ser
    130                 135                 140

Ala Ser Gln Ser Pro Pro Leu Ser Cys Ala Val Pro Ser Asn Asp Ser
145                 150                 155                 160

Ser Pro Ile Tyr Ser Ala Ala Pro Thr Phe Pro Thr Pro Asn Thr Asp
                165                 170                 175

Ile Phe Pro Glu Pro Gln Ser Gln Ala Phe Pro Gly Ser Ala Gly Thr
            180                 185                 190

Ala Leu Gln Tyr Pro Pro Pro Ala Tyr Pro Ala Thr Lys Gly Gly Phe
            195                 200                 205

Gln Val Pro Met Ile Pro Asp Tyr Leu Phe Pro Gln Gln Gly Asp
    210                 215                 220

Leu Ser Leu Gly Thr Pro Asp Gln Lys Pro Phe Gln Gly Leu Glu Asn
225                 230                 235                 240

Arg Thr Gln Gln Pro Ser Leu Thr Pro Leu Ser Thr Ile Lys Ala Phe
                245                 250                 255

Ala Thr Gln Ser Gly Ser Gln Asp Leu Lys Ala Leu Asn Thr Thr Tyr
            260                 265                 270

Gln Ser Gln Leu Ile Lys Pro Ser Arg Met Arg Lys Tyr Pro Asn Arg
        275                 280                 285

Pro Ser Lys Thr Pro Pro His Glu Arg Pro Tyr Ala Cys Pro Val Glu
    290                 295                 300

Ser Cys Asp Arg Arg Phe Ser Arg Ser Asp Glu Leu Thr Arg His Ile
305                 310                 315                 320

Arg Ile His Thr Gly Gln Lys Pro Phe Gln Cys Arg Ile Cys Met Arg
                325                 330                 335

Asn Phe Ser Arg Ser Asp His Leu Thr Thr His Ile Arg Thr His Thr
            340                 345                 350

Gly Glu Lys Pro Phe Ala Cys Asp Ile Cys Gly Arg Lys Phe Ala Arg
        355                 360                 365

Ser Asp Glu Arg Lys Arg His Thr Lys Ile His Leu Arg Gln Lys Asp
    370                 375                 380
```

| | | | | | | | | | | | | | | | |
|---|---|---|---|---|---|---|---|---|---|---|---|---|---|---|---|
| Lys | Lys | Ala | Asp | Lys | Ser | Val | Val | Ala | Ser | Pro | Ala | Ala | Ser | Ser | Leu |
| 385 | | | | 390 | | | | | 395 | | | | | | 400 |
| Ser | Ser | Tyr | Pro | Ser | Pro | Val | Ala | Thr | Ser | Tyr | Pro | Ser | Pro | Ala | Thr |
| | | | | 405 | | | | | 410 | | | | | 415 | |
| Thr | Ser | Phe | Pro | Ser | Pro | Val | Pro | Thr | Ser | Tyr | Ser | Ser | Pro | Gly | Ser |
| | | | 420 | | | | | 425 | | | | | 430 | | |
| Ser | Thr | Tyr | Pro | Ser | Pro | Ala | His | Ser | Gly | Phe | Pro | Ser | Pro | Ser | Val |
| | | 435 | | | | | 440 | | | | | 445 | | | |
| Ala | Thr | Thr | Phe | Ala | Ser | Val | Pro | Pro | Ala | Phe | Pro | Thr | Gln | Val | Ser |
| | 450 | | | | | 455 | | | | | 460 | | | | |
| Ser | Phe | Pro | Ser | Ala | Gly | Val | Ser | Ser | Ser | Phe | Ser | Thr | Ser | Thr | Gly |
| 465 | | | | | 470 | | | | | 475 | | | | | 480 |
| Leu | Ser | Asp | Met | Thr | Ala | Thr | Phe | Ser | Pro | Arg | Thr | Ile | Glu | Ile | Cys |
| | | | | 485 | | | | | 490 | | | | | 495 | |

( 2 ) INFORMATION FOR SEQ ID NO:3:

( i ) SEQUENCE CHARACTERISTICS:
( A ) LENGTH: 3132 base pairs
( B ) TYPE: nucleic acid
( C ) STRANDEDNESS: double
( D ) TOPOLOGY: linear ( x i ) SEQUENCE DESCRIPTION: SEQ ID NO:3:

| | | | | | |
|---|---|---|---|---|---|
| CCGCAGAACT | TGGGGAGCCG | CCGCCGCCAT | CCGCCGCCGC | AGCCAGCTTC | CGCCGCCGCA | 60 |
| GGACCGGCCC | CTGCCCCAGC | CTCCGCAGCC | GCGGCGCGTC | CACGCCCGCC | CGCGCCCAGG | 120 |
| GCGAGTCGGG | GTCGCCGCCT | GCACGCTTCT | CAGTGTTCCC | CGCGCCCCGC | ATGTAACCCG | 180 |
| GCCAGGCCCC | CGCAACGGTG | TCCCCTGCAG | CTCCAGCCCC | GGGCTGCACC | CCCCCGCCCC | 240 |
| GACACCAGCT | CTCCAGCCTG | CTCGTCCAGG | ATGGCCGCGG | CCAAGGCCGA | GATGCAGCTG | 300 |
| ATGTCCCCGC | TGCAGATCTC | TGACCCGTTC | GGATCCTTTC | CTCACTCGCC | CACCATGGAC | 360 |
| AACTACCCTA | AGCTGGAGGA | GATGATGCTG | CTGAGCAACG | GGGCTCCCCA | GTTCCTCGGC | 420 |
| GCCGCCGGGG | CCCCAGAGGG | CAGCGGCAGC | AACAGCAGCA | GCAGCAGCAG | CGGGGGCGGT | 480 |
| GGAGGCGGCG | GGGGCGGCAG | CAACAGCAGC | AGCAGCAGCA | GCACCTTCAA | CCCTCAGGCG | 540 |
| GACACGGGCG | AGCAGCCCTA | CGAGCACCTG | ACCGCAGAGT | CTTTTCCTGA | CATCTCTCTG | 600 |
| AACAACGAGA | AGGTGCTGGT | GGAGACCAGT | TACCCCAGCC | AAACCACTCG | ACTGCCCCCC | 660 |
| ATCACCTATA | CTGGCCGCTT | TTCCCTGGAG | CCTGCACCCA | ACAGTGGCAA | CACCTTGTGG | 720 |
| CCCGAGCCCC | TCTTCAGCTT | GGTCAGTGGC | CTAGTGAGCA | TGACCAACCC | ACCGGCCTCC | 780 |
| TCGTCCTCAG | CACCATCTCC | AGCGGCCTCC | TCCGCCTCCG | CCTCCCAGAG | CCCACCCCTG | 840 |
| AGCTGCGCAG | TGCCATCCAA | CGACAGCAGT | CCCATTTACT | CAGCGGCACC | CACCTTCCCC | 900 |
| ACGCCGAACA | CTGACATTTT | CCCTGAGCCA | CAAAGCCAGG | CCTTCCCGGG | CTCGGCAGGG | 960 |
| ACAGCGCTCC | AGTACCCGCC | TCCTGCCTAC | CCTGCCGCCA | AGGGTGGCTT | CCAGGTTCCC | 1020 |
| ATGATCCCCG | ACTACCTGTT | TCCACAGCAG | CAGGGGGATC | TGGGCCTGGG | CACCCCAGAC | 1080 |
| CAGAAGCCCT | TCCAGGGCCT | GGAGAGCCGC | ACCCAGCAGC | CTTCGCTAAC | CCCTCTGTCT | 1140 |
| ACTATTAAGG | CCTTTGCCAC | TCAGTCGGGC | TCCCAGGACC | TGAAGGCCCT | CAATACCAGC | 1200 |
| TACCAGTCCC | AGCTCATCAA | ACCCAGCCGC | ATGCGCAAGT | ATCCCAACCG | GCCCAGCAAG | 1260 |
| ACGCCCCCC | ACGAACGCCC | TTACGCTTGC | CCAGTGGAGT | CCTGTGATCG | CCGCTTCTCC | 1320 |
| CGCTCCGACG | AGCTCACCCG | CCACATCCGC | ATCCACACAG | GCCAGAAGCC | CTTCCAGTGC | 1380 |
| CGCATCTGCA | TGCGCAACTT | CAGCCGCAGC | GACCACCTCA | CCACCCACAT | CCGCACCCAC | 1440 |

| | | | | | |
|---|---|---|---|---|---|
| ACAGGCGAAA | AGCCCTTCGC | CTGCGACATC | TGTGGAAGAA | AGTTTGCCAG | GAGCGATGAA | 1500 |
| CGCAAGAGGC | ATACCAAGAT | CCACTTGCGG | CAGAAGGACA | AGAAAGCAGA | CAAAGTGTT | 1560 |
| GTGGCCTCTT | CGGCCACCTC | CTCTCTCTCT | TCCTACCCGT | CCCCGGTTGC | TACCTCTTAC | 1620 |
| CCGTCCCCGG | TTACTACCTC | TTATCCATCC | CCGGCCACCA | CCTCATACCC | ATCCCTGTG | 1680 |
| CCCACCTCCT | TCTCCTCTCC | CGGCTCCTCG | ACCTACCCAT | CCCTGTGCA | CAGTGGCTTC | 1740 |
| CCCTCCCCGT | CGGTGGCCAC | CACGTACTCC | TCTGTTCCCC | CTGCTTTCCC | GGCCCAGGTC | 1800 |
| AGCAGCTTCC | CTTCCTCAGC | TGTCACCAAC | TCCTTCAGCG | CCTCCACAGG | GCTTTCGGAC | 1860 |
| ATGACAGCAA | CCTTTTCTCC | CAGGACAATT | GAAATTTGCT | AAAGGGAAAG | GGGAAAGAAA | 1920 |
| GGGAAAAGGG | AGAAAAAGAA | ACACAAGAGA | CTTAAAGGAC | AGGAGGAGGA | GATGGCCATA | 1980 |
| GGAGAGGAGG | GTTCCTCTTA | GGTCAGATGG | AGGTTCTCAG | AGCCAAGTCC | TCCCTCTCTA | 2040 |
| CTGGAGTGGA | AGGTCTATTG | GCCAACAATC | CTTTCTGCCC | ACTTCCCCTT | CCCCAATTAC | 2100 |
| TATTCCCTTT | GACTTCAGCT | GCCTGAAACA | GCCATGTCCA | AGTTCTTCAC | CTCTATCCAA | 2160 |
| AGAACTTGAT | TTGCATGGAT | TTTGGATAAA | TCATTTCAGT | ATCATCTCCA | TCATATGCCT | 2220 |
| GACCCCTTGC | TCCCTTCAAT | GCTAGAAAAT | CGAGTTGGCA | AAATGGGGTT | TGGGCCCCTC | 2280 |
| AGAGCCCTGC | CCTGCACCCT | TGTACAGTGT | CTGTGCCATG | GATTTCGTTT | TTCTTGGGGT | 2340 |
| ACTCTTGATG | TGAAGATAAT | TTGCATATTC | TATTGTATTA | TTTGGAGTTA | GGTCCTCACT | 2400 |
| TGGGGGAAAA | AAAAAAAAAA | AAGCCAAGCA | AACCAATGGT | GATCCTCTAT | TTTGTGATGA | 2460 |
| TGCTGTGACA | ATAAGTTTGA | ACCTTTTTTT | TTGAAACAGC | AGTCCCAGTA | TTCTCAGAGC | 2520 |
| ATGTGTCAGA | GTGTTGTTCC | GTTAACCTTT | TTGTAAATAC | TGCTTGACCG | TACTCTCACA | 2580 |
| TGTGGCAAAA | TATGGTTTGG | TTTTTCTTTT | TTTTTTTGA | AAGTGTTTTT | TCTTCGTCCT | 2640 |
| TTTGGTTTAA | AAAGTTTCAC | GTCTTGGTGC | CTTTTGTGTG | ATGCCCCTTG | CTGATGGCTT | 2700 |
| GACATGTGCA | ATTGTGAGGG | ACATGCTCAC | CTCTAGCCTT | AAGGGGGGCA | GGGAGTGATG | 2760 |
| ATTTGGGGGA | GGCTTTGGGA | GCAAAATAAG | GAAGAGGGCT | GAGCTGAGCT | TCGGTTCTCC | 2820 |
| AGAATGTAAG | AAAACAAAAT | CTAAAACAAA | ATCTGAACTC | TCAAAAGTCT | ATTTTTTTAA | 2880 |
| CTGAAAATGT | AAATTTATAA | ATATATTCAG | GAGTTGGAAT | GTTGTAGTTA | CCTACTGAGT | 2940 |
| AGGCGGCGAT | TTTTGTATGT | TATGAACATG | CAGTTCATTA | TTTTGTGGTT | CTATTTTACT | 3000 |
| TTGTACTTGT | GTTTGCTTAA | ACAAAGTGAC | TGTTTGGCTT | ATAAACACAT | TGAATGCGCT | 3060 |
| TTATTGCCCA | TGGGATATGT | GGTGTATATC | CTTCCAAAAA | ATTAAAACGA | AAATAAAGTA | 3120 |
| GCTGCGATTG | GG | | | | | 3132 |

( 2 ) INFORMATION FOR SEQ ID NO:4:

( i ) SEQUENCE CHARACTERISTICS:
( A ) LENGTH: 543 amino acids
( B ) TYPE: amino acid
( D ) TOPOLOGY: linear ( x i ) SEQUENCE DESCRIPTION: SEQ ID NO:4:

```
Met Ala Ala Ala Lys Ala Glu Met Gln Leu Met Ser Pro Leu Gln Ile
 1               5                  10                  15

Ser Asp Pro Phe Gly Ser Phe Pro His Ser Pro Thr Met Asp Asn Tyr
            20                  25                  30

Pro Lys Leu Glu Glu Met Met Leu Leu Ser Asn Gly Ala Pro Gln Phe
        35                  40                  45

Leu Gly Ala Ala Gly Ala Pro Glu Gly Ser Gly Ser Asn Ser Ser Ser
    50                  55                  60
```

|  |  |  |  |  |  |  |  |  |  |  |  |  |  |  |
|---|---|---|---|---|---|---|---|---|---|---|---|---|---|---|
| Ser 65 | Ser | Ser | Gly | Gly 70 | Gly | Gly | Gly | Gly | Gly 75 | Gly | Ser | Asn | Ser | Ser 80 |
| Ser | Ser | Ser | Ser | Thr 85 | Phe | Asn | Pro | Gln 90 | Ala | Asp | Thr | Gly | Glu 95 | Gln Pro |
| Tyr | Glu | His | Leu 100 | Thr | Ala | Glu | Ser 105 | Phe | Pro | Asp | Ile | Ser 110 | Leu | Asn Asn |
| Glu | Lys | Val 115 | Leu | Val | Glu | Thr | Ser 120 | Tyr | Pro | Ser | Gln | Thr 125 | Thr | Arg Leu |
| Pro | Pro 130 | Ile | Thr | Tyr | Thr | Gly 135 | Arg | Phe | Ser | Leu | Glu 140 | Pro | Ala | Pro Asn |
| Ser 145 | Gly | Asn | Thr | Leu | Trp 150 | Pro | Glu | Pro | Leu | Phe 155 | Ser | Leu | Val | Ser Gly 160 |
| Leu | Val | Ser | Met | Thr 165 | Asn | Pro | Pro | Ala | Ser 170 | Ser | Ser | Ser | Ala | Pro Ser 175 |
| Pro | Ala | Ala | Ser 180 | Ser | Ala | Ser | Ala | Ser 185 | Gln | Ser | Pro | Pro | Leu 190 | Ser Cys |
| Ala | Val | Pro 195 | Ser | Asn | Asp | Ser | Ser 200 | Pro | Ile | Tyr | Ser | Ala 205 | Ala | Pro Thr |
| Phe | Pro 210 | Thr | Pro | Asn | Thr | Asp 215 | Ile | Phe | Pro | Glu | Pro 220 | Gln | Ser | Gln Ala |
| Phe 225 | Pro | Gly | Ser | Ala | Gly 230 | Thr | Ala | Leu | Gln | Tyr 235 | Pro | Pro | Pro | Ala Tyr 240 |
| Pro | Ala | Ala | Lys | Gly 245 | Gly | Phe | Gln | Val | Pro 250 | Met | Ile | Pro | Asp | Tyr Leu 255 |
| Phe | Pro | Gln | Gln 260 | Gln | Gly | Asp | Leu | Gly 265 | Leu | Gly | Thr | Pro | Asp 270 | Gln Lys |
| Pro | Phe | Gln 275 | Gly | Leu | Glu | Ser | Arg 280 | Thr | Gln | Gln | Pro | Ser 285 | Leu | Thr Pro |
| Leu | Ser 290 | Thr | Ile | Lys | Ala | Phe 295 | Ala | Thr | Gln | Ser | Gly 300 | Ser | Gln | Asp Leu |
| Lys 305 | Ala | Leu | Asn | Thr | Ser 310 | Tyr | Gln | Ser | Gln | Leu 315 | Ile | Lys | Pro | Ser Arg 320 |
| Met | Arg | Lys | Tyr | Pro 325 | Asn | Arg | Pro | Ser | Lys 330 | Thr | Pro | Pro | His | Glu Arg 335 |
| Pro | Tyr | Ala | Cys 340 | Pro | Val | Glu | Ser | Cys 345 | Asp | Arg | Arg | Phe | Ser 350 | Arg Ser |
| Asp | Glu | Leu 355 | Thr | Arg | His | Ile | Arg 360 | Ile | His | Thr | Gly | Gln 365 | Lys | Pro Phe |
| Gln | Cys 370 | Arg | Ile | Cys | Met | Arg 375 | Asn | Phe | Ser | Arg | Ser 380 | Asp | His | Leu Thr |
| Thr 385 | His | Ile | Arg | Thr | His 390 | Thr | Gly | Glu | Lys | Pro 395 | Phe | Ala | Cys | Asp Ile 400 |
| Cys | Gly | Arg | Lys | Phe 405 | Ala | Arg | Ser | Asp | Glu 410 | Arg | Lys | Arg | His | Thr Lys 415 |
| Ile | His | Leu | Arg 420 | Gln | Lys | Asp | Lys | Lys 425 | Ala | Asp | Lys | Ser | Val 430 | Val Ala |
| Ser | Ser | Ala 435 | Thr | Ser | Ser | Leu | Ser 440 | Ser | Tyr | Pro | Ser | Pro 445 | Val | Ala Thr |
| Ser | Tyr 450 | Pro | Ser | Pro | Val | Thr 455 | Thr | Ser | Tyr | Pro | Ser 460 | Pro | Ala | Thr Thr |
| Ser 465 | Tyr | Pro | Ser | Pro | Val 470 | Pro | Thr | Ser | Phe | Ser 475 | Ser | Pro | Gly | Ser Ser 480 |
| Thr | Tyr | Pro | Ser | Pro | Val | His | Ser | Gly | Phe | Pro | Ser | Pro | Ser | Val Ala |

```
                                  485                        490                        495
            Thr  Thr  Tyr  Ser  Ser  Val  Pro  Pro  Ala  Phe  Pro  Ala  Gln  Val  Ser  Ser
                          500                        505                       510

Phe  Pro  Ser  Ser  Ala  Val  Thr  Asn  Ser  Phe  Ser  Ala  Ser  Thr  Gly  Leu
                          515                        520                       525

Ser  Asp  Met  Thr  Ala  Thr  Phe  Ser  Pro  Arg  Thr  Ile  Glu  Ile  Cys
                          530                        535                       540
```

( 2 ) INFORMATION FOR SEQ ID NO:5:

( i ) SEQUENCE CHARACTERISTICS:
        ( A ) LENGTH: 1440 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 57..1422

( x i ) SEQUENCE DESCRIPTION: SEQ ID NO:5:

```
TCTGACACTC  CAGGTAGCGA  GGGAGTTGGG  TCTCCAGGTT  GTGCGAGGAG  CAAATG                        56

ATG  ACC  GCC  AAG  GCC  GTA  GAC  AAA  ATC  CCA  GTA  ACT  CTC  AGT  GGT  TTT           104
Met  Thr  Ala  Lys  Ala  Val  Asp  Lys  Ile  Pro  Val  Thr  Leu  Ser  Gly  Phe
 1                    5                        10                       15

GTG  CAC  CAG  CTG  TCT  GAC  AAC  ATC  TAC  CCG  GTG  GAG  GAC  CTC  GCC  GCC           152
Val  His  Gln  Leu  Ser  Asp  Asn  Ile  Tyr  Pro  Val  Glu  Asp  Leu  Ala  Ala
               20                        25                        30

ACG  TCG  GTG  ACC  ATC  TTT  CCC  AAT  GCC  GAA  CTG  GGA  GGC  CCC  TTT  GAC           200
Thr  Ser  Val  Thr  Ile  Phe  Pro  Asn  Ala  Glu  Leu  Gly  Gly  Pro  Phe  Asp
               35                        40                        45

CAG  ATG  AAC  GGA  GTG  GCC  GGA  GAT  GGC  ATG  ATC  AAC  ATT  GAC  ATG  ACT           248
Gln  Met  Asn  Gly  Val  Ala  Gly  Asp  Gly  Met  Ile  Asn  Ile  Asp  Met  Thr
          50                        55                        60

GGA  GAG  AAG  AGG  TCG  TTG  GAT  CTC  CCA  TAT  CCC  AGC  AGC  TTT  GCT  CCC           296
Gly  Glu  Lys  Arg  Ser  Leu  Asp  Leu  Pro  Tyr  Pro  Ser  Ser  Phe  Ala  Pro
 65                        70                        75                        80

GTC  TCT  GCA  CCT  AGA  AAC  CAG  ACC  TTC  ACT  TAC  ATG  GGC  AAG  TTC  TCC           344
Val  Ser  Ala  Pro  Arg  Asn  Gln  Thr  Phe  Thr  Tyr  Met  Gly  Lys  Phe  Ser
                    85                        90                        95

ATT  GAC  CCA  CAG  TAC  CCT  GGT  GCC  AGC  TGC  TAC  CCA  GAA  GGC  ATA  ATC           392
Ile  Asp  Pro  Gln  Tyr  Pro  Gly  Ala  Ser  Cys  Tyr  Pro  Glu  Gly  Ile  Ile
                    100                       105                       110

AAT  ATT  GTG  AGT  GCA  GGC  ATC  TTG  CAA  GGG  GTC  ACT  TCC  CCA  GCT  TCA           440
Asn  Ile  Val  Ser  Ala  Gly  Ile  Leu  Gln  Gly  Val  Thr  Ser  Pro  Ala  Ser
               115                       120                       125

ACC  ACA  GCC  TCA  TCC  AGC  GTC  ACC  TCT  GCC  TCC  CCC  AAC  CCA  CTG  GCC           488
Thr  Thr  Ala  Ser  Ser  Ser  Val  Thr  Ser  Ala  Ser  Pro  Asn  Pro  Leu  Ala
     130                       135                       140

ACA  GGA  CCC  CTG  GGT  GTG  TGC  ACC  ATG  TCC  CAG  ACC  CAG  CCT  GAC  CTG           536
Thr  Gly  Pro  Leu  Gly  Val  Cys  Thr  Met  Ser  Gln  Thr  Gln  Pro  Asp  Leu
145                       150                       155                       160

GAC  CAC  CTG  TAC  TCT  CCG  CCA  CCG  CCT  CCT  CCT  CCT  TAT  TCT  GGC  TGT           584
Asp  His  Leu  Tyr  Ser  Pro  Pro  Pro  Pro  Pro  Pro  Pro  Tyr  Ser  Gly  Cys
                    165                       170                       175

GCA  GGA  GAC  CTC  TAC  CAG  GAC  CCT  TCT  GCG  TTC  CTG  TCA  GCA  GCC  ACC           632
Ala  Gly  Asp  Leu  Tyr  Gln  Asp  Pro  Ser  Ala  Phe  Leu  Ser  Ala  Ala  Thr
                    180                       185                       190

ACC  TCC  ACC  TCT  TCC  TCT  CTG  GCC  TAC  CCA  CCA  CCT  CCT  TCC  TAT  CCA           680
Thr  Ser  Thr  Ser  Ser  Ser  Leu  Ala  Tyr  Pro  Pro  Pro  Pro  Ser  Tyr  Pro
               195                       200                       205
```

| | | | | | | | | | | | | | | | |
|---|---|---|---|---|---|---|---|---|---|---|---|---|---|---|---|
| TCC | CCC | AAG | CCA | GCC | ACG | GAC | CCA | GGT | CTC | TTC | CCA | ATG | ATC | CCA | GAC | 728 |
| Ser | Pro | Lys | Pro | Ala | Thr | Asp | Pro | Gly | Leu | Phe | Pro | Met | Ile | Pro | Asp | |
| 210 | | | | | 215 | | | | | | 220 | | | | | |
| TAT | CCT | GGA | TTC | TTT | CCA | TCT | CAG | TGC | CAG | AGA | GAC | CTA | CAT | GGT | ACA | 776 |
| Tyr | Pro | Gly | Phe | Phe | Pro | Ser | Gln | Cys | Gln | Arg | Asp | Leu | His | Gly | Thr | |
| 225 | | | | | 230 | | | | 235 | | | | | 240 | | |
| GCT | GGC | CCA | GAC | CGT | AAG | CCC | TTT | CCC | TGC | CCA | CTG | GAC | ACC | CTG | CGG | 824 |
| Ala | Gly | Pro | Asp | Arg | Lys | Pro | Phe | Pro | Cys | Pro | Leu | Asp | Thr | Leu | Arg | |
| | | | | 245 | | | | | 250 | | | | 255 | | | |
| GTG | CCC | CCT | CCA | CTC | ACT | CCA | CTC | TCT | ACA | ATC | CGT | AAC | TTT | ACC | CTG | 872 |
| Val | Pro | Pro | Pro | Leu | Thr | Pro | Leu | Ser | Thr | Ile | Arg | Asn | Phe | Thr | Leu | |
| | | | 260 | | | | | 265 | | | | | 270 | | | |
| GGG | GGC | CCC | AGT | GCT | GGG | ATG | ACC | GGA | CCA | GGG | GCC | AGT | GGA | GGC | AGC | 920 |
| Gly | Gly | Pro | Ser | Ala | Gly | Met | Thr | Gly | Pro | Gly | Ala | Ser | Gly | Gly | Ser | |
| | | 275 | | | | | 280 | | | | | 285 | | | | |
| GAG | GGA | CCC | CGG | CTG | CCT | GGT | AGC | AGC | TCA | GCA | GCA | GCA | GCA | GCC | GCC | 968 |
| Glu | Gly | Pro | Arg | Leu | Pro | Gly | Ser | Ser | Ser | Ala | Ala | Ala | Ala | Ala | Ala | |
| | 290 | | | | | 295 | | | | | 300 | | | | | |
| GCC | GCC | GCC | GCC | TAT | AAC | CCA | CAC | CAC | CTG | CCA | CTG | CGG | CCC | ATT | CTG | 1016 |
| Ala | Ala | Ala | Ala | Tyr | Asn | Pro | His | His | Leu | Pro | Leu | Arg | Pro | Ile | Leu | |
| 305 | | | | | 310 | | | | | 315 | | | | | 320 | |
| AGG | CCT | CGC | AAG | TAC | CCC | AAC | AGA | CCC | AGC | AAG | ACG | CCG | GTG | CAC | GAG | 1064 |
| Arg | Pro | Arg | Lys | Tyr | Pro | Asn | Arg | Pro | Ser | Lys | Thr | Pro | Val | His | Glu | |
| | | | | 325 | | | | | 330 | | | | | 335 | | |
| AGG | CCC | TAC | CCG | TGC | CCA | GCA | GAA | GGC | TGC | GAC | CGG | CGG | TTC | TCC | CGC | 1112 |
| Arg | Pro | Tyr | Pro | Cys | Pro | Ala | Glu | Gly | Cys | Asp | Arg | Arg | Phe | Ser | Arg | |
| | | | 340 | | | | | 345 | | | | | 350 | | | |
| TCT | GAC | GAG | CTG | ACA | CGG | CAC | ATC | CGA | ATC | CAC | ACT | GGG | CAT | AAG | CCC | 1160 |
| Ser | Asp | Glu | Leu | Thr | Arg | His | Ile | Arg | Ile | His | Thr | Gly | His | Lys | Pro | |
| | | 355 | | | | | 360 | | | | | 365 | | | | |
| TTC | CAG | TGT | CGG | ATC | TGC | ATG | CGC | AAC | TTC | AGC | CGC | AGT | GAC | CAC | CTC | 1208 |
| Phe | Gln | Cys | Arg | Ile | Cys | Met | Arg | Asn | Phe | Ser | Arg | Ser | Asp | His | Leu | |
| | 370 | | | | | 375 | | | | | 380 | | | | | |
| ACC | ACC | CAT | ATC | CGC | ACC | CAC | ACC | GGT | GAG | AAG | CCC | TTC | GCC | TGT | GAC | 1256 |
| Thr | Thr | His | Ile | Arg | Thr | His | Thr | Gly | Glu | Lys | Pro | Phe | Ala | Cys | Asp | |
| 385 | | | | | 390 | | | | | 395 | | | | | 400 | |
| TAC | TGT | GGC | CGA | AAG | TTT | GCC | CGG | AGT | GAT | GAG | AGG | AAG | CGC | CAC | ACC | 1304 |
| Tyr | Cys | Gly | Arg | Lys | Phe | Ala | Arg | Ser | Asp | Glu | Arg | Lys | Arg | His | Thr | |
| | | | | 405 | | | | | 410 | | | | | 415 | | |
| AAG | ATC | CAC | CTG | AGA | CAG | AAA | GAG | CGG | AAA | AGC | AGT | GCC | CCC | TCT | GCA | 1352 |
| Lys | Ile | His | Leu | Arg | Gln | Lys | Glu | Arg | Lys | Ser | Ser | Ala | Pro | Ser | Ala | |
| | | | 420 | | | | | 425 | | | | | 430 | | | |
| TCG | GTG | CCA | GCC | CCC | TCT | ACA | GCC | TCC | TGC | TCT | GGG | GGC | GTG | CAG | GCC | 1400 |
| Ser | Val | Pro | Ala | Pro | Ser | Thr | Ala | Ser | Cys | Ser | Gly | Gly | Val | Gln | Ala | |
| | | 435 | | | | | 440 | | | | | 445 | | | | |
| TGG | GGG | TAC | CCT | GTG | CAG | CAG | T | AACAGCAGCA | | GTCTTGGC | | | | | | 1440 |
| Trp | Gly | Tyr | Pro | Val | Gln | Gln | | | | | | | | | | |
| | 450 | | | | | 455 | | | | | | | | | | |

( 2 ) INFORMATION FOR SEQ ID NO:6:

( i ) SEQUENCE CHARACTERISTICS:
        ( A ) LENGTH: 455 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | | |
|---|---|---|---|---|---|---|---|---|---|---|---|---|---|---|---|
| Met | Thr | Ala | Lys | Ala | Val | Asp | Lys | Ile | Pro | Val | Thr | Leu | Ser | Gly | Phe |
| 1 | | | | 5 | | | | | 10 | | | | | 15 | |
| Val | His | Gln | Leu | Ser | Asp | Asn | Ile | Tyr | Pro | Val | Glu | Asp | Leu | Ala | Ala |

|          |          |          |          |          | 20       |          |          |          |          | 25       |          |          |          |          | 30       |          |          |          |          |
|---|---|---|---|---|---|---|---|---|---|---|---|---|---|---|---|---|---|---|---|

Thr Ser Val Thr Ile Phe Pro Asn Ala Glu Leu Gly Gly Pro Phe Asp
        35                    40                 45

Gln Met Asn Gly Val Ala Gly Asp Gly Met Ile Asn Ile Asp Met Thr
     50                 55                60

Gly Glu Lys Arg Ser Leu Asp Leu Pro Tyr Pro Ser Ser Phe Ala Pro
65                70            75                80

Val Ser Ala Pro Arg Asn Gln Thr Phe Thr Tyr Met Gly Lys Phe Ser
            85             90              95

Ile Asp Pro Gln Tyr Pro Gly Ala Ser Cys Tyr Pro Glu Gly Ile Ile
       100            105            110

Asn Ile Val Ser Ala Gly Ile Leu Gln Gly Val Thr Ser Pro Ala Ser
       115            120            125

Thr Thr Ala Ser Ser Ser Val Thr Ser Ala Ser Pro Asn Pro Leu Ala
130               135            140

Thr Gly Pro Leu Gly Val Cys Thr Met Ser Gln Thr Gln Pro Asp Leu
145               150            155           160

Asp His Leu Tyr Ser Pro Pro Pro Pro Pro Pro Tyr Ser Gly Cys
             165            170           175

Ala Gly Asp Leu Tyr Gln Asp Pro Ser Ala Phe Leu Ser Ala Ala Thr
       180            185            190

Thr Ser Thr Ser Ser Ser Leu Ala Tyr Pro Pro Pro Ser Tyr Pro
        195             200            205

Ser Pro Lys Pro Ala Thr Asp Pro Gly Leu Phe Pro Met Ile Pro Asp
    210                215            220

Tyr Pro Gly Phe Phe Pro Ser Gln Cys Gln Arg Asp Leu His Gly Thr
225               230            235           240

Ala Gly Pro Asp Arg Lys Pro Phe Pro Cys Pro Leu Asp Thr Leu Arg
            245           250            255

Val Pro Pro Pro Leu Thr Pro Leu Ser Thr Ile Arg Asn Phe Thr Leu
            260           265            270

Gly Gly Pro Ser Ala Gly Met Thr Gly Pro Gly Ala Ser Gly Gly Ser
       275            280            285

Glu Gly Pro Arg Leu Pro Gly Ser Ser Ala Ala Ala Ala Ala Ala
    290                295            300

Ala Ala Ala Ala Tyr Asn Pro His His Leu Pro Leu Arg Pro Ile Leu
305               310            315           320

Arg Pro Arg Lys Tyr Pro Asn Arg Pro Ser Lys Thr Pro Val His Glu
            325           330            335

Arg Pro Tyr Pro Cys Pro Ala Glu Gly Cys Asp Arg Arg Phe Ser Arg
       340            345            350

Ser Asp Glu Leu Thr Arg His Ile Arg Ile His Thr Gly His Lys Pro
       355            360            365

Phe Gln Cys Arg Ile Cys Met Arg Asn Phe Ser Arg Ser Asp His Leu
    370                375            380

Thr Thr His Ile Arg Thr His Thr Gly Glu Lys Pro Phe Ala Cys Asp
385               390            395           400

Tyr Cys Gly Arg Lys Phe Ala Arg Ser Asp Glu Arg Lys Arg His Thr
            405           410            415

Lys Ile His Leu Arg Gln Lys Glu Arg Lys Ser Ser Ala Pro Ser Ala
            420           425            430

Ser Val Pro Ala Pro Ser Thr Ala Ser Cys Ser Gly Gly Val Gln Ala
       435            440            445

```
Trp Gly Tyr Pro Val Gln Gln
    450                 455
```

(2) INFORMATION FOR SEQ ID NO:7:

(i) SEQUENCE CHARACTERISTICS:
        (A) LENGTH: 2850 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 358..1519

(xi) SEQUENCE DESCRIPTION: SEQ ID NO:7:

```
GATCAATACT GAGGCCGCGT CGACCCCCTT GAGCCGAGAC CCCCCCCCAG CCCAGCCCCC        60

ACCCCACCCC CCGCACACGC CCCACCCCCC CCACGACCCA GCCTCATACC GCACCAGCTG       120

AGGCACCCAA GAGGATTACC CCCTGGGGCC CTCTCCCGCC CCCCAAAAAA GAGAAGATCC       180

CCTCTCCTGG CCCATCCCTT CCCTTCTTCC CTCCCCCCTC CCCCCGAACT TTCCCTCTCG       240

CATGCTTTTC CCCTGCACCA CGGATCGCCT CTCGGATGCC GCTTGCCTGG AAGCTGCGTT       300

AGGAGCGAGC GGCGGCGGTG GCGGCGGTGG CGGCGGCGGC GGCAGCTCGG GAGTGCT         357

ATG ACC GGC AAA CTC GCC GAG AAG CTG CCG GTG ACC ATG AGC AGT TTG        405
Met Thr Gly Lys Leu Ala Glu Lys Leu Pro Val Thr Met Ser Ser Leu
 1               5                  10                 15

CTA AAC CAA CTG CCT GAC AAT CTG TAC CCC GAG GAG ATC CCC AGC GCG        453
Leu Asn Gln Leu Pro Asp Asn Leu Tyr Pro Glu Glu Ile Pro Ser Ala
             20                  25                  30

CTC AAC CTC TTC TCC GGC AGC AGC GAC TCG GTA GTC CAT TAC AAT CAG        501
Leu Asn Leu Phe Ser Gly Ser Ser Asp Ser Val Val His Tyr Asn Gln
         35                  40                  45

ATG GCT ACA GAG AAT GTA ATG GAC ATC GGT CTG ACC AAC GAG AAG CCC        549
Met Ala Thr Glu Asn Val Met Asp Ile Gly Leu Thr Asn Glu Lys Pro
     50                  55                  60

AAC CCG GAA CTC TCT TAC TCC GGC TCC TTC CAG CCA GCC CCC GGG AAC        597
Asn Pro Glu Leu Ser Tyr Ser Gly Ser Phe Gln Pro Ala Pro Gly Asn
 65                  70                  75                  80

AAG ACC GTG ACC TAC TTG GGA AAG TTC GCC TTC GAC TCC CCT TCC AAC        645
Lys Thr Val Thr Tyr Leu Gly Lys Phe Ala Phe Asp Ser Pro Ser Asn
                 85                  90                  95

TGG TGC CAG GAC AAC ATC ATT AGC CTC ATG AGC GCC GGC ATC TTG GGG        693
Trp Cys Gln Asp Asn Ile Ile Ser Leu Met Ser Ala Gly Ile Leu Gly
             100                 105                 110

GTG CCC CCG GCT TCA GGG GCG CTA AGC ACG CAG ACG TCC ACG GCC AGC        741
Val Pro Pro Ala Ser Gly Ala Leu Ser Thr Gln Thr Ser Thr Ala Ser
         115                 120                 125

ATG GTG CAG CCA CCG CAG GGT GAC GTG GAG GCC ATG TAT CCC GCG CTA        789
Met Val Gln Pro Pro Gln Gly Asp Val Glu Ala Met Tyr Pro Ala Leu
     130                 135                 140

CCC CCC TAC TCC AAC TGC GGC GAC CTC TAC TCA GAG CCC GTG TCT TTC        837
Pro Pro Tyr Ser Asn Cys Gly Asp Leu Tyr Ser Glu Pro Val Ser Phe
145                 150                 155                 160

CAC GAC CCC CAG GGC AAT CCC GGG CTC GCC TAT TCC CCC CAG GAT TAC        885
His Asp Pro Gln Gly Asn Pro Gly Leu Ala Tyr Ser Pro Gln Asp Tyr
                 165                 170                 175

CAA TCG GCC AAG CCG GCG TTG GAC AGC AAT CTC TTC CCC ATG ATT CCT        933
Gln Ser Ala Lys Pro Ala Leu Asp Ser Asn Leu Phe Pro Met Ile Pro
             180                 185                 190

GAC TAC AAC CTC TAC CAC CAC CCC AAC GAC ATG GGC TCC ATT CCG GAG        981
Asp Tyr Asn Leu Tyr His His Pro Asn Asp Met Gly Ser Ile Pro Glu
```

```
                        195                              200                                205
CAC   AAG   CCC   TTC   CAG   GGC   ATG   GAC   CCC   ATC   CGG   GTC   AAC   CCG   CCC   CCT        1029
His   Lys   Pro   Phe   Gln   Gly   Met   Asp   Pro   Ile   Arg   Val   Asn   Pro   Pro   Pro
      210                           215                           220

ACT   ACC   CCT   CTG   GAG   ACC   ATC   AAG   GCA   TTC   AAA   GAC   AAG   CAG   ATC   CAC        1077
Thr   Thr   Pro   Leu   Glu   Thr   Ile   Lys   Ala   Phe   Lys   Asp   Lys   Gln   Ile   His
225                     230                           235                                 240

CCG   GGC   TTT   GGC   AGC   CTG   CCC   CAG   CCG   CGG   CTC   ACC   CTC   AAG   CCC   ATC        1125
Pro   Gly   Phe   Gly   Ser   Leu   Pro   Gln   Pro   Arg   Leu   Thr   Leu   Lys   Pro   Ile
                        245                           250                           255

CGG   CCC   CGC   AAG   TAC   CCC   AAC   CGG   CCT   AGC   AAG   ACA   CCG   CTC   CAC   GAA        1173
Arg   Pro   Arg   Lys   Tyr   Pro   Asn   Arg   Pro   Ser   Lys   Thr   Pro   Leu   His   Glu
                  260                           265                           270

CGG   CCC   CAC   GCG   TGC   CCG   GCC   GAG   GGC   TGC   GAC   CGC   CGT   TTC   AGC   CGT        1221
Arg   Pro   His   Ala   Cys   Pro   Ala   Glu   Gly   Cys   Asp   Arg   Arg   Phe   Ser   Arg
            275                           280                           285

TCG   GAC   GAG   CTG   ACC   CGG   CAC   CTG   CGC   ATC   CAC   ACG   GGC   CAC   AAG   CCC        1269
Ser   Asp   Glu   Leu   Thr   Arg   His   Leu   Arg   Ile   His   Thr   Gly   His   Lys   Pro
      290                           295                           300

TTC   CAG   TGC   CGG   ATC   TGC   ATG   CGG   AGC   TTC   AGC   CGC   AGC   GAC   CAC   CTC        1317
Phe   Gln   Cys   Arg   Ile   Cys   Met   Arg   Ser   Phe   Ser   Arg   Ser   Asp   His   Leu
305                     310                           315                                 320

ACC   ACT   CAC   ATC   CGC   ACT   CAT   ACG   GGC   GAG   AAG   CCC   TTT   GCC   TGC   GAG        1365
Thr   Thr   His   Ile   Arg   Thr   His   Thr   Gly   Glu   Lys   Pro   Phe   Ala   Cys   Glu
                        325                           330                           335

TTC   TGC   GGG   CGC   AAG   TTT   GCG   CGC   AGC   GAC   GAG   CGC   AAG   CGC   CAC   GCC        1413
Phe   Cys   Gly   Arg   Lys   Phe   Ala   Arg   Ser   Asp   Glu   Arg   Lys   Arg   His   Ala
                  340                           345                           350

AAG   ATC   CAC   CTC   AAG   CAA   AAG   GAG   AAG   AAG   GCG   GAG   AAG   GGC   GGT   GCA        1461
Lys   Ile   His   Leu   Lys   Gln   Lys   Glu   Lys   Lys   Ala   Glu   Lys   Gly   Gly   Ala
            355                           360                           365

CCC   TCT   GCA   TCC   TCG   GCG   CCC   CCC   GTG   TCG   CTG   GCC   CCC   GTG   GTC   ACC        1509
Pro   Ser   Ala   Ser   Ser   Ala   Pro   Pro   Val   Ser   Leu   Ala   Pro   Val   Val   Thr
      370                           375                           380

ACC   TGC   GCC   T   GAGGATCGGG   CCCCCAGATC   CCCACTTTTC   CCCTCCAGTG                             1559
Thr   Cys   Ala
385

CCTCCCGGCT   GCTAGCCTGA   AAGCAGCGGG   AAAGCCAGCC   ACGGAGGCGT   AGGGGCCGCG                         1619

CCCTGGCCTC   TCCATGGACG   TGCGGCCCCT   TGCTTCCCCT   TCGATGCCCC   CGGTTCCCAA                         1679

CCTTTCACGC   CGGCCAGCGG   TCAGGGGCCA   GGGCTGGAGG   CGCCTTCCCC   TCGCGGTCCC                         1739

CCACTTAGCC   AAGGCGTGGG   GGCGGAAAGG   TGGCGTCTAG   CCCGCTTTGT   TCAGTTCGGA                         1799

TCGCCTTGAT   CCAGGGGCCG   CCGGGCCGCG   CCAAGGACCT   GCAAGGGACT   GAAGGCGGAG                         1859

CCCATCCAAC   CCTCGCCCGA   CCCAAACACC   TCATTGTTTC   CCCCACGTCT   CCCTCTATAC                         1919

CCCCTCGAAG   ACTCGAGAGG   GGGAGGGGGT   AAGGAGCGCA   CCAAAGCGCA   GAGCTTGCTG                         1979

CCCGCCGCAC   GCACGCGCGC   CTGCGTGCGG   GGATGCGCGC   GAGTGTGTGC   GTGCTCGCGT                         2039

GTGTGTGTAT   GTGTGTGTGT   GAGTGTGTGT   GTGTGCGCGC   GCGCAAGCGT   GTGTGTTTAA                         2099

GACTCTTGAG   CTGAACTGGG   CTGTGTTTAC   CCCAAACTCT   TCCCCACCTC   GGGTCCCCAA                         2159

GCCGCTGGGA   GATGTCCCAT   GCTGGGGGTC   CGCACGTGGC   TGGAGGAGGT   GGTCTTCCAT                         2219

CCGCTCTGAA   ATCATGTTTC   TTAGAGAAAT   GCCTCGGATG   CCGCCGACGC   GGTGCTGCTG                         2279

CCGCCGCTTC   GGGTTTGGCC   CCTCAGAACC   CCTCCTTTTC   TGAGCGCTTC   CCTCTTAGGC                         2339

CTCAGGGCAG   TTTGATCTGT   GGGGAGAAAG   AGCAGCCATC   GCTGAGCCTG   CCTTTTAAAA                         2399

TATATGTGTA   TTTCCTTAGC   CCCACTCTAA   GAAATCTATG   TTCCTGAGTT   TGCCCCCTGC                         2459
```

```
CCTCCCACTC  CTTCCCCTTT  TCCCCTCTAA  ACCTTCTCCC  ATCTCTTTCA  AAATCTTTTC    2519

CCAGAAAGGC  AGGCTTCAAC  CAGCCACTCC  AGCTTTGTGT  CTTCTCTCAA  TTACATAGCA    2579

ATTTCTCCTT  CCCACCATCA  TGGGGAAGCT  GGCTCTGCTT  TTGCCCTTTG  TCATCACCAA    2639

CACAACAGAT  AGAATTTAAA  TATAAGTATA  TGGTGTGCGT  GTGTATGTAT  GTGTATGTAT    2699

ATGCATGCAT  GTGTATAAAG  ATGCACATGC  GTACATATAC  ATAACATACA  CACAATATGT    2759

ATTCCTAGCA  AAATAAAATC  TCTAAGGTAC  TTGGTTATCC  AGTGCAGTGC  ACCGGAATAA    2819

AGAGAATTTG  TAGGCGTATA  CAGCTTTAAA  T                                     2850
```

( 2 ) INFORMATION FOR SEQ ID NO:8:

( i ) SEQUENCE CHARACTERISTICS:
        ( A ) LENGTH: 387 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Thr  Gly  Lys  Leu  Ala  Glu  Lys  Leu  Pro  Val  Thr  Met  Ser  Ser  Leu
 1              5                        10                       15

Leu  Asn  Gln  Leu  Pro  Asp  Asn  Leu  Tyr  Pro  Glu  Glu  Ile  Pro  Ser  Ala
               20                        25                       30

Leu  Asn  Leu  Phe  Ser  Gly  Ser  Ser  Asp  Ser  Val  Val  His  Tyr  Asn  Gln
               35                        40                       45

Met  Ala  Thr  Glu  Asn  Val  Met  Asp  Ile  Gly  Leu  Thr  Asn  Glu  Lys  Pro
          50                        55                   60

Asn  Pro  Glu  Leu  Ser  Tyr  Ser  Gly  Ser  Phe  Gln  Pro  Ala  Pro  Gly  Asn
65                        70                        75                       80

Lys  Thr  Val  Thr  Tyr  Leu  Gly  Lys  Phe  Ala  Phe  Asp  Ser  Pro  Ser  Asn
                    85                        90                       95

Trp  Cys  Gln  Asp  Asn  Ile  Ile  Ser  Leu  Met  Ser  Ala  Gly  Ile  Leu  Gly
                    100                       105                      110

Val  Pro  Pro  Ala  Ser  Gly  Ala  Leu  Ser  Thr  Gln  Thr  Ser  Thr  Ala  Ser
               115                       120                      125

Met  Val  Gln  Pro  Pro  Gln  Gly  Asp  Val  Glu  Ala  Met  Tyr  Pro  Ala  Leu
          130                       135                      140

Pro  Pro  Tyr  Ser  Asn  Cys  Gly  Asp  Leu  Tyr  Ser  Glu  Pro  Val  Ser  Phe
145                      150                       155                      160

His  Asp  Pro  Gln  Gly  Asn  Pro  Gly  Leu  Ala  Tyr  Ser  Pro  Gln  Asp  Tyr
                    165                       170                      175

Gln  Ser  Ala  Lys  Pro  Ala  Leu  Asp  Ser  Asn  Leu  Phe  Pro  Met  Ile  Pro
               180                       185                      190

Asp  Tyr  Asn  Leu  Tyr  His  His  Pro  Asn  Asp  Met  Gly  Ser  Ile  Pro  Glu
          195                       200                      205

His  Lys  Pro  Phe  Gln  Gly  Met  Asp  Pro  Ile  Arg  Val  Asn  Pro  Pro  Pro
     210                       215                      220

Thr  Thr  Pro  Leu  Glu  Thr  Ile  Lys  Ala  Phe  Lys  Asp  Lys  Gln  Ile  His
225                      230                       235                      240

Pro  Gly  Phe  Gly  Ser  Leu  Pro  Gln  Pro  Pro  Leu  Thr  Leu  Lys  Pro  Ile
                    245                       250                      255

Arg  Pro  Arg  Lys  Tyr  Pro  Asn  Arg  Pro  Ser  Lys  Thr  Pro  Leu  His  Glu
               260                       265                      270

Arg  Pro  His  Ala  Cys  Pro  Ala  Glu  Gly  Cys  Asp  Arg  Arg  Phe  Ser  Arg
          275                       280                      285
```

```
Ser  Asp  Glu  Leu  Thr  Arg  His  Leu  Arg  Ile  His  Thr  Gly  His  Lys  Pro
     290                      295                     300

Phe  Gln  Cys  Arg  Ile  Cys  Met  Arg  Ser  Phe  Ser  Arg  Ser  Asp  His  Leu
305                      310                     315                      320

Thr  Thr  His  Ile  Arg  Thr  His  Thr  Gly  Glu  Lys  Pro  Phe  Ala  Cys  Glu
                    325                      330                     335

Phe  Cys  Gly  Arg  Lys  Phe  Ala  Arg  Ser  Asp  Glu  Arg  Lys  Arg  His  Ala
               340                      345                     350

Lys  Ile  His  Leu  Lys  Gln  Lys  Glu  Lys  Lys  Ala  Glu  Lys  Gly  Gly  Ala
          355                      360                     365

Pro  Ser  Ala  Ser  Ser  Ala  Pro  Pro  Val  Ser  Leu  Ala  Pro  Val  Val  Thr
     370                      375                     380

Thr  Cys  Ala
385
```

( 2 ) INFORMATION FOR SEQ ID NO:9:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GCGGGGGCG                                                             9

( 2 ) INFORMATION FOR SEQ ID NO:10:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GCGWGGGCG                                                            9

( 2 ) INFORMATION FOR SEQ ID NO:11:

( i ) SEQUENCE CHARACTERISTICS:
        ( A ) LENGTH: 109 amino acids
        ( B ) TYPE: amino acid
        ( D ) TOPOLOGY: linear ( x i ) SEQUENCE DESCRIPTION: SEQ ID NO:11:

```
Arg  Gly  Gly  Lys  Cys  Ser  Thr  Arg  Cys  Phe  Cys  Pro  Arg  Pro  His  Ala
1              5                      10                     15

Lys  Ala  Phe  Ala  Cys  Pro  Val  Glu  Ser  Cys  Val  Arg  Ser  Phe  Ala  Arg
               20                      25                     30

Ser  Asp  Glu  Leu  Asn  Arg  His  Leu  Arg  Ile  His  Thr  Gly  His  Lys  Pro
          35                      40                     45

Phe  Gln  Cys  Arg  Ile  Cys  Leu  Arg  Asn  Phe  Ser  Arg  Ser  Asp  His  Leu
     50                      55                     60

Thr  Thr  His  Val  Arg  Thr  His  Thr  Gly  Glu  Lys  Pro  Phe  Ala  Cys  Asp
65                       70                     75                       80

Val  Cys  Gly  Arg  Arg  Phe  Ala  Arg  Ser  Asp  Glu  Lys  Lys  Arg  His  Ser
               85                      90                     95

Lys  Val  His  Leu  Arg  Gln  Lys  Ala  Arg  Ala  Glu  Glu  Arg
                    100                     105
```

( 2 ) INFORMATION FOR SEQ ID NO:12:

```
( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GATCTCGCGG    GGGCGAGGGG    GATC                                              2 4
```

We claim:

1. A method for inhibiting the growth of a tumor in a mammal, wherein said growth is induced by the mitogenic activity of PDGF, comprising directly administering to said tumor a retroviral vector comprising an expression control sequence operatively linked to a nucleic acid sequence encoding a mammalian EGR-1 polypeptide, a nucleic acid sequence encoding a fragment of a mammalian EGR-1 polypeptide comprising the zinc finger domain or a nucleic acid sequence that both hybridizes to any of the foregoing nucleic acid sequences under standard hybridization conditions and also encodes a polypeptide that inhibits the mitogenic activity of PDGF, wherein the nucleic acid sequence is expressed in the cells of said tumor in an amount sufficient to inhibit the growth of said cells.

2. The method of claim 1, wherein the tumor is selected from the group consisting of an osteosarcoma, a fibrosarcoma, a glioblastoma and a breast carcinoma.

3. The method of claim 1, wherein the mammalian EGR-1 is human EGR-1 or mouse EGR-1.

4. The method of claim 1, wherein the nucleic acid sequence encodes a fragment of a mammalian EGR-1 polypeptide comprising the zinc finger domain.

5. The method of claim 1, wherein the nucleic acid sequence encodes a fragment of a mammalian EGR-1 polypeptide consisting essentially of the zinc finger domain.

6. The method of claim 1, wherein the nucleic acid sequence encodes a fragment of a mammalian EGR-1 polypeptide consisting essentially of the zinc finger domain and the remainder of the carboxy-terminal end.

7. The method of claim 1, wherein the expression control sequence comprises an RSV promoter or a CMV promoter.

8. A method for inhibiting the growth of a tumor cell in vitro, wherein said growth is induced by the mitogenic activity of PDGF, comprising transfecting said tumor cell with a retroviral vector comprising an expression control sequence operatively linked to a nucleic acid sequence encoding a mammalian EGR-1 polypeptide, a nucleic acid sequence encoding a fragment of a mammalian EGR-1 polypeptide comprising the zinc finger domain or a nucleic acid sequence that both hybridizes to any of the foregoing nucleic acid sequences under standard hybridization conditions and also encodes a polypeptide that inhibits the mitogenic activity of PDGF, wherein the nucleic acid sequence is expressed in said tumor cell in an amount sufficient to inhibit the growth of said tumor cell.

9. The method of claim 8, wherein the tumor cell is a cell selected from the group consisting of a human fibrosarcoma cell, a human osteosarcoma cell, a human glioblastoma cell, a human breast carcinoma cell and a v-sis-transformed NIH 3T3 cell.

* * * * *